US012768908B2

(12) United States Patent
Agostinelli et al.

(10) Patent No.: US 12,768,908 B2
(45) Date of Patent: Oct. 20, 2026

(54) SUSCEPTIBILITY PROBES FOR DETECTING SURGICAL MARKERS

(71) Applicant: ENDOMAGNETICS LTD, Cambridge (GB)

(72) Inventors: Tiziano Agostinelli, Cambridge (GB); Jonathan Edward Isaac, Cambridge (GB); Liam Douglas Malone, Cambridge (GB)

(73) Assignee: ENDOMAGNETICS LTD (GB)

( * ) Notice: Subject to any disclaimer, the term of this patent is extended or adjusted under 35 U.S.C. 154(b) by 0 days.

(21) Appl. No.: 18/853,991

(22) PCT Filed: Apr. 5, 2023

(86) PCT No.: PCT/GB2023/050910
§ 371 (c)(1),
(2) Date: Oct. 3, 2024

(87) PCT Pub. No.: WO2023/194728
PCT Pub. Date: Oct. 12, 2023

(65) Prior Publication Data
US 2025/0213324 A1 Jul. 3, 2025

(30) Foreign Application Priority Data
Apr. 5, 2022 (GB) ...................................... 2204998

(51) Int. Cl.
*G01R 33/00* (2006.01)
*A61B 5/06* (2006.01)
(Continued)

(52) U.S. Cl.
CPC .......... *G01R 33/0017* (2013.01); *A61B 5/062* (2013.01); *G01R 33/022* (2013.01); *A61B 90/39* (2016.02)

(58) Field of Classification Search
CPC ...... G01R 33/0017; G01R 33/12; A61B 5/05; A61B 5/06
See application file for complete search history.

(56) References Cited

U.S. PATENT DOCUMENTS

| | | | | |
|---|---|---|---|---|
| 3,445,928 A * | 5/1969 | Beynon | G01R 33/05 | 335/297 |
| 4,380,735 A * | 4/1983 | Bell | G01R 33/025 | 324/225 |

(Continued)

FOREIGN PATENT DOCUMENTS

| | | |
|---|---|---|
| JP | 2005091203 A | 4/2005 |
| JP | 2007068967 A | 3/2007 |

(Continued)

OTHER PUBLICATIONS

U.S. Appl. No. 61/777,928, filed Jan. 23, 2001, Govari et al.

(Continued)

*Primary Examiner* — Anh Tuan T Nguyen
*Assistant Examiner* — Younhee Choi
(74) *Attorney, Agent, or Firm* — K&L GATES LLP

(57) ABSTRACT

A probe for locating a magnetic marker for use in surgery. The probe comprises at least two first coils (3*a*, 3*b*) and at least one second coil (5) which are arranged substantially coaxially on a longitudinal axis of the probe for measuring the proximity of a magnetic marker to the probe, and a baseline voltage taring device (7) comprising a first elongate conductor which defines a conducting path extending partially around the probe axis. The conducting path is configured and arranged such that in use the balancing magnetic field induces a balancing voltage in a sense coil that at least partially offsets the baseline voltage. Also disclosed is a method of manufacturing such a probe, a method of setting up such a probe for use in sensing a magnetic marker, and (Continued)

detection apparatus for locating a magnetic marker during surgery.

18 Claims, 9 Drawing Sheets

(51) Int. Cl.
*G01R 33/022* (2006.01)
*A61B 90/00* (2016.01)

(56) References Cited

U.S. PATENT DOCUMENTS

| | | | | |
|---|---|---|---|---|
| 6,538,432 | B1 * | 3/2003 | Bacon | G01R 33/14 324/228 |
| 7,372,261 | B2 * | 5/2008 | Choi | G01R 33/04 324/249 |
| 8,174,259 | B2 | 5/2012 | Hattersley et al. | |
| 8,757,166 | B2 | 6/2014 | McKenna et al. | |
| 8,968,171 | B2 | 3/2015 | McKenna et al. | |
| 9,234,877 | B2 | 1/2016 | Hattersley et al. | |
| 9,239,314 | B2 | 1/2016 | Hattersley et al. | |
| 9,427,186 | B2 | 8/2016 | Hattersley et al. | |
| 9,523,748 | B2 | 12/2016 | Hattersley et al. | |
| 9,682,247 | B2 | 6/2017 | Susedik et al. | |
| 9,687,668 | B2 | 6/2017 | McKenna et al. | |
| 9,808,539 | B2 | 11/2017 | Shawcross et al. | |
| 10,124,186 | B2 | 11/2018 | McKenna et al. | |
| 10,595,957 | B2 | 3/2020 | Mayes et al. | |
| 10,634,741 | B2 | 4/2020 | Hattersley | |
| 11,191,612 | B2 | 12/2021 | Agostinelli et al. | |
| 11,592,501 | B2 | 2/2023 | Hattersley | |
| 11,660,160 | B2 | 5/2023 | Agostinelli et al. | |
| 12,193,806 | B2 | 1/2025 | Harmer et al. | |
| 12,207,915 | B2 | 1/2025 | Harmer et al. | |
| 12,290,348 | B2 | 5/2025 | Agostinelli et al. | |
| 12,544,184 | B2 | 2/2026 | Udale et al. | |
| 2009/0201016 | A1 * | 8/2009 | Hattersley | G01R 33/1215 324/239 |
| 2012/0229130 | A1 | 9/2012 | Hattersely et al. | |
| 2013/0066194 | A1 * | 3/2013 | Seter | A61B 5/062 29/846 |
| 2019/0280650 | A1 * | 9/2019 | Deak | H03D 7/14 |
| 2021/0267065 | A1 * | 8/2021 | Florendo | H01F 41/041 |
| 2022/0313476 | A1 | 10/2022 | Harmer et al. | |
| 2023/0346251 | A1 | 11/2023 | Harmer et al. | |
| 2025/0025260 | A1 | 1/2025 | Udale et al. | |
| 2025/0064548 | A1 | 2/2025 | Mayes et al. | |
| 2025/0143732 | A1 | 5/2025 | Profit | |
| 2025/0213324 | A1 | 7/2025 | Agostinelli et al. | |
| 2025/0228620 | A1 | 7/2025 | Hattersley | |
| 2025/0241554 | A1 | 7/2025 | Harmer et al. | |
| 2025/0255693 | A1 | 8/2025 | Udale et al. | |

FOREIGN PATENT DOCUMENTS

| | | | |
|---|---|---|---|
| JP | 2016517289 | A | 6/2016 |
| JP | 6334418 | B2 | 5/2018 |
| JP | 2018526160 | A | 9/2018 |
| JP | 2019146957 | A | 9/2019 |
| WO | 2011067576 | A1 | 6/2011 |
| WO | 2014140566 | A1 | 9/2014 |

OTHER PUBLICATIONS

Waanders, S. et al.; "A handheld SPIO-based sentinel lymph node mapping device using differential magnetometry"; Physics in Medicine & Biology; Institute of Physics and Engineering in Medicine; vol. 61; (2016); pp. 8120-8134.

Combined Search and Examination Report under Sections 17 & 18(3) for GB Patent Application No. GB2204998.5; date of report Oct. 3, 2022; (2 pages).

PCT International Search Report and PCT Written Opinion for PCT International Application No. PCT/GB2023/050910; date of mailing Jul. 4, 2023; (18 pages).

English translation of Japanese Office Action dated Mar. 11, 2026 for Japanese Patent Application No. 2024-558357, (7 pages).

* cited by examiner

SUSCEPTIBILITY PROBES FOR DETECTING SURGICAL MARKERS

CROSS REFERENCE TO RELATED APPLICATIONS

This is the national phase under 35 U.S.C. § 371 of International Application No. PCT/GB2023/050910 filed on Apr. 5, 2023, which claims priority to and the benefit of United Kingdom Patent Application No. 2204998.5 filed on Apr. 5, 2022, the entire disclosures of which are incorporated by reference herein.

TECHNICAL FIELD

The present disclosure relates to a probe for sensing an implanted magnetic marker in surgery, and a method of manufacturing such a probe, a method of setting up such a probe and a detection system comprising such a probe.

BACKGROUND

In the field of susceptibility probes for the detection of implantable magnetic markers for use in locating lesions and the like during surgery, it is known to use a combination of drive coils and sense coils to determine the proximity of a magnetic marker (also called a seed) relative to the probe. A current is supplied to a drive coil, thereby generating a driving magnetic field. The driving magnetic field induces a response from the magnetic marker, which, in turn, induces a sense voltage in a sense coil. By measuring and interpreting the sense voltage from the sense coil, the position of the marker relative to the probe may be determined. However, a voltage is also be induced in the sense coil from the drive coil. This can interfere with determination of the location of the marker, as a voltage induced in the sense coil from the drive coil masks the sense voltage resulting from the marker.

In known surgical probes, such for example as disclosed by WO 2014/140567 A2, a coil arrangement is used that enables voltages induced directly from drive coils to be cancelled out, such that the sense voltage can be attributed to the magnetic marker. This is achieved, for example, by arranging a drive coil at a midpoint between two similar sense coils that are connected in anti-series or have opposite windings. Alternatively, a single sense coil may be interposed between two drive coils.

Owing to manufacturing tolerances for the probes and the coils, it may not be practical accurately to cancel out or eliminate entirely voltage induced in one or more sense coils directly from one or more drive coils. For example, two particular sense or drive coils may not be identical to one another or the positioning of the drive and sense coils may be insufficiently precise. As a result, there may be a residual baseline voltage induced in the one or more sense coils as a result of the one or more drive coils: this can be problematic for accurate determination of a marker's position. While it is generally desirable for a probe to have a narrow diameter to reduce the size of surgical incision that is required when using the probe, this problem is compounded in probes with small coils, because in such probes, even small changes in coil position or drive current result in relatively large changes in drive field and therefore also in sensed voltage.

There is therefore a need for an improved susceptibility probe that allows for more accurate determination of marker position, even with a smaller probe diameter, without interference from one or more drive coils.

SUMMARY OF DISCLOSURE

According to a first aspect of the present disclosure, there is provided a probe for sensing an implanted magnetic marker for use in a surgical procedure. The probe comprises at least two first coils and at least one second coil which are arranged to form a gradiometer for measuring the proximity of the magnetic marker to the probe. The at least two first coils are one of either sense coils or drive coils. The at least one second coil is the other of a drive coil or sense coil. The one or more drive coils are adapted for connection to a current source to generate driving magnetic fields through the drive coils in use. Meanwhile, the one or more sense coils are adapted for connection to a signal processor for processing one or more sense voltages induced in the respective one or more sense coils in use to generate an output signal which may represent the distance between the marker and the probe.

Suitably, the first or second coils may be configured or arranged to minimise a baseline voltage component of a sense voltage induced in the one or more sense coils that is attributable directly to the driving magnetic field. For example, in some embodiments, as described herein, at least two drive coils, or at least two sense coils, may be connected in anti-series to one another or they may be connected in series but have windings in opposite directions, thereby to minimise a baseline voltage component of the sense voltage.

Alternatively, two or more sense coils may be arranged to output to the signal processor separate sense voltages to allow the signal processor to process the sense voltages to minimise a baseline voltage component of the sense voltages that is attributable directly to the driving magnetic field. For example, the signal processor may be operable to subtract the sense voltage from one sense coil from the sense voltage from another sense coil to substantially remove a component of the sense voltage that is attributable directly to the driving magnetic field.

After minimising the baseline voltage, some baseline voltage may remain in the sense voltage owing to manufacturing tolerances or for other reasons. In accordance with the present disclosure, the probe further comprises a baseline voltage taring device which comprises a first elongate conductor defining a conducting path extending partially around a longitudinal axis defined by the probe (the "probe axis") proximate the one or more sense coils. Suitably, the first conductor is disposed at a fixed location on the probe axis. The first conductor is suitably arcuate, preferably forming an arc of circle in a plane perpendicular to the probe axis. The conducting path thus extends azimuthally but incompletely around the probe axis. The first conductor is adapted for connection to a current source to generate a balancing magnetic field in the vicinity of the one or more sense coils. The azimuthal length of the conducting path about the probe axis is such that in operation the balancing magnetic field induces a balancing voltage in the one or more sense coils that at least partially offsets any residual baseline voltage, so that the sense voltage is at least predominantly attributable to a response field generated by the marker in response to the driving field, which corresponds to the proximity of the marker.

According to a second aspect, the present disclosure provides a method of manufacturing a probe for sensing a magnetic marker. The method may suitably comprise mounting at least two first coils and at least one second coil substantially coaxially on a longitudinal axis of the probe. The at least two first coils are one of sense coils or drive coils. The at least one second coil is the other of a drive coil or sense coil. The one or more drive coils are mounted such that they are connectable to a current source to generate a driving magnetic field through the one or more drive coils. The one or more sense coils are mounted such that they are connectable to a signal processor.

As described above, the first or second coils may be configured or arranged to minimise a baseline voltage component of a sense voltage induced in the one or more sense coils that is attributable directly to the driving magnetic field. Alternatively, two or more sense coils may be arranged to output to the signal processor separate sense voltages to allow the signal processor to process the sense voltages to minimise a baseline voltage component of the sense voltages that is attributable directly to the driving magnetic field. The first and second coils are thus mounted to the probe such that they are configured and arranged to serve as a gradiometer for measuring the proximity of a magnetic marker to the probe.

In accordance with the present disclosure, the method further comprises fitting to the probe a baseline voltage taring device comprising a first elongate conductor which defines a conducting path that extends partially around the probe axis juxtaposed the one or more sense coils. The taring device is mounted such that the first conductor is connectable to a current source to generate a balancing magnetic field in the vicinity of the one or more sense coils in use. The baseline taring device may be fitted juxtaposed the one or more sense coils, i.e. adjacent to, or near to the one or more sense coils, such that when the first conductor is connected to a current source the taring device generates a balancing magnetic field in the vicinity of the one or more sense coils. In some implementations, the baseline taring device may be fitted adjacent to the one or one of the sense coils. In some implementations, a drive coil may be interposed between the baseline taring device and the or at least one of the sense coils. Those skilled in the art will understand that the at least two first coils and at least one second coil may typically be arranged to generate a magnetic field in use that has substantial reflectional symmetry about a transverse plane passing through a midpoint on the longitudinal axis of the probe. The first elongate conductor may suitably be positioned off-centre with respect to the midpoint, such that the magnetic field produced by the baseline taring device is asymmetrical about the midpoint. The azimuthal extent of the conducting path around the probe axis is such that the balancing magnetic field induces a balancing voltage in the one or more sense coils which at least partially offsets the baseline voltage. In use therefore, the sense voltage is at least predominantly attributable to a response field generated by the marker in response to the driving field, which corresponds to the proximity of the marker.

The signal processor may be configured to generate an output signal such, for example, as an audio, haptic and/or display signal representing the distance between the marker and the probe.

Suitably, the method of the present disclosure comprises adjusting the azimuthal length of the conducting path around the probe axis to minimise the baseline voltage across the one or more sense coils.

According to a third aspect, the present disclosure therefore provides a method of setting up a probe for sensing a magnetic marker during surgery. The probe suitably comprises at least two first coils and at least one second coil which are arranged substantially coaxially on a longitudinal axis of the probe as a gradiometer for measuring the proximity of a magnetic marker to the probe. The at least two first coils are one of either sense coils or drive coils. The at least one second coil is the other of a drive coil or sense coil. The one or more drive coils are adapted for connection to a current source to generate a driving magnetic field. The one or more sense coils are adapted for connection to a signal processor for receiving and processing a sense voltage induced in the one or more sense coils to generate an output signal. As described above, the first or second coils may be configured or arranged to minimise a baseline voltage component of a sense voltage induced in the one or more sense coils that is attributable directly to the driving magnetic field. Alternatively, two or more sense coils may be arranged to output to the signal processor separate sense voltages to allow the signal processor to process the sense voltages to minimise a baseline voltage component of the sense voltages that is attributable directly to the driving magnetic field. The probe further comprises a baseline voltage taring device comprising a first elongate conductor defining a conducting path which extends at least partially around the probe axis juxtaposed the one or more sense coils. The first conductor is connectable to a current source to generate a balancing magnetic field in the vicinity of the one or more sense coils.

The method of setting up the probe comprises taring the balancing magnetic field by adjusting the azimuthal length of the conducting path around the probe axis to control the balancing voltage to minimise or substantially eliminate the baseline voltage in the one or more sense coils. In some embodiments, the azimuthal length of the conducting path may be adjusted by connecting the first conductor to the current source at circumferentially spaced locations thereon, such that the azimuthal length of the conducting path corresponds to the length of the first conductor intermediate the spaced locations. Suitably, the length of the conducting path around the probe axis may then be fixed.

According to a fourth aspect, the present disclosure comprises detection apparatus for locating a magnetic marker during surgery, the apparatus comprising a probe according to the first aspect of the present disclosure, at least one current source which is selectively operable to generate a driving magnetic field through the one or more drive coils and the conducting path, and at least one signal processor which is configured to receive at least one sense voltage from the one or more sense coils and generate an output signal representing the distance between the probe and a magnetic marker. In some embodiments, the apparatus may further comprise at least one magnetic marker.

It will be appreciated that features described in relation to one aspect of the present disclosure may be incorporated into other aspects of the present disclosure. For example, the methods of the disclosure may incorporate features described with reference to the probe and/or apparatus of the disclosure and vice versa.

DESCRIPTION OF THE FIGURES

Embodiments of the present disclosure are described below by way of example only with reference to the accompanying drawings in which:

FIG. 6(*b*) is a plan view of the taring device shown in FIG. 6(*a*) in an un-coiled configuration for ease of reference;

FIGS. 8(*b*)-8(*d*) are perspective views of coil arrangements of probes according to different respective embodiments of the present disclosure, showing schematically different taring devices that extend azimuthally around the probe axis to different extents;

DETAILED DESCRIPTION

Figure 1:
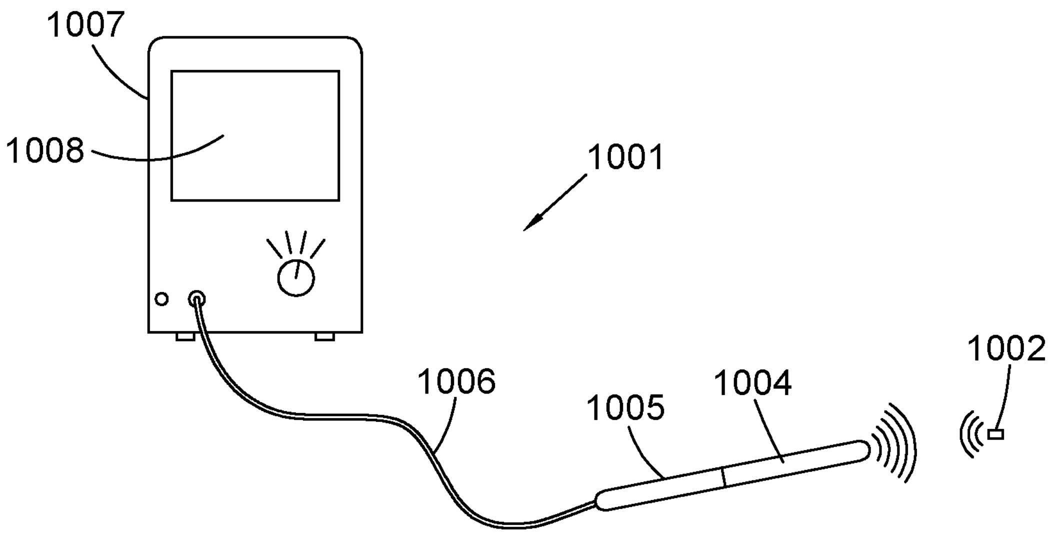
FIG. 1 is a schematic drawing of a general arrangement of a susceptometry probe and base station for use in detecting a magnetic marker in surgery.
Figure 2:
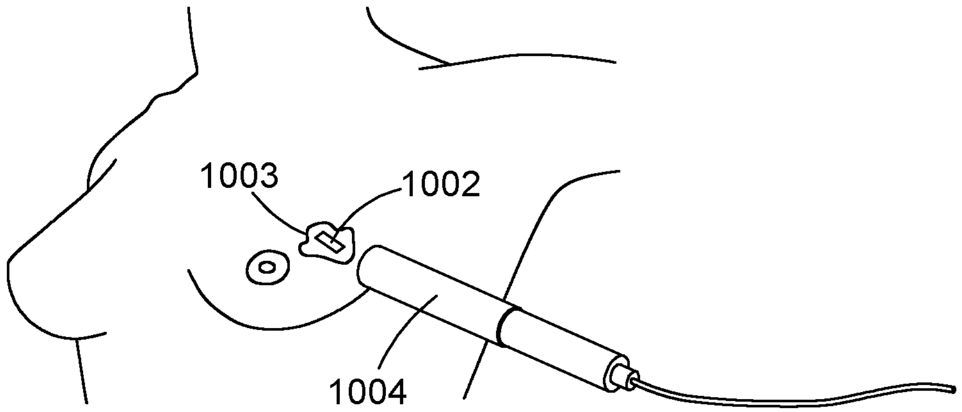
FIG. 2 is a schematic drawing showing use of a susceptometry probe for localising a magnetic marker which is implanted in a breast to mark a lesion.

As illustrated in FIGS. 1 and 2 of the accompanying drawings, detection apparatus 1001 for use in surgery to localise an implantable magnetic marker 1002 that is used to mark a non-palpable lesion (i.e. one that is too small to feel or see during surgery) typically comprises a probe 1004 which connected to a base station 1007. The probe 1004 suitably comprises a handheld wand 1005 and may be connected via a suitable cable 1006 to the base station 1007 as shown, or it may be connected wirelessly. As shown in FIG. 2, the probe 1004 is used during surgery to guide the surgeon to the lesion 1003 and allow accurate excision of the lesion while minimising the amount of healthy tissue that is removed.

The marker 1002 suitably comprises one or more pieces of magnetic material. Suitable markers 1002 are disclosed by WO 2016/193753 A2, for example. The probe 1004 typically comprises at least one drive coil for generating a driving magnetic field, which produces a response field from the marker, and at least one sense coil for detecting the response field from the marker. The response field produces a sense voltage in the sense coil, which is detected by a suitable signal processor housed in the base station 1007. A known probe is disclosed by WO 2014/140567 A2. The sense voltage corresponds to the distance between the marker 1002 and the probe 1004. The signal processor is thus configured, as disclosed by WO 2011/067576 A1, for example, to calculate the marker distance from the detected sense voltage. The signal processor may generate an output signal which represents the marker distance. The output signal may be a display signal, e.g. for displaying the marker distance on a screen 1008 on the base station 1007, or an audio or haptic signal, for example as disclosed by WO 2022/008922 A1.

The present disclosure provides improvements in and relating to probes of the kind described above.

According to a first aspect, therefore, the present disclosure provides a probe for locating a magnetic marker for use in surgery, the probe comprising:

at least two first coils and at least one second coil which are arranged substantially coaxially on a longitudinal axis of the probe as a gradiometer for measuring the proximity of a magnetic marker to the probe; the at least two first coils being one of either sense coils or drive coils, and the at least one second coil being the other of a drive coil or sense coil; the one or more drive coils being adapted for connection to a current source to generate a driving magnetic field, and the one or more sense coils being adapted for connection to a signal processor for processing one or more sense voltages induced in the respective one or more sense coils to generate an output signal representing the distance between the marker and the probe; the first or second coils being configured or arranged to minimise a baseline voltage component of the sense voltage induced in the one or more sense coils that is attributable directly to the driving magnetic field or to output to the signal processor separate sense voltages from two or more sense coils to allow the signal processor to process the sense voltages to minimise a baseline voltage component of the sense voltages that is attributable directly to the driving magnetic field; and a baseline voltage taring device comprising a first elongate conductor which defines a conducting path extending partially around the probe axis, and is connectable to a current source to generate a balancing magnetic field in the vicinity of the one or more sense coils;

wherein the conducting path is configured and arranged such that in use the balancing magnetic field induces a balancing voltage in the one or more sense coils that at least partially offsets the baseline voltage; whereby the sense voltage is at least predominantly attributable to a response field generated by the marker in response to the driving field, which corresponds to the proximity of the marker.

Suitably, the at least two first coils and the at least one second coil may be centred on the longitudinal axis of the probe (the "probe axis"). The coils may be separated from one another along the probe axis. The first elongate conductor may extend partially around the probe axis juxtaposed the one or more sense coils. Typically, the first elongate conductor may be positioned off-centre with respect to the at least two first coils and the at least one second coil.

The at least two first coils and the at least one second coil may suitably be contained within a hollow probe housing. The probe housing may have an elongated shape. In some embodiments, the probe housing may be substantially cylindrical in shape. In some embodiments, the probe housing may comprise a plurality of segments of the same or different outer diameters. The probe housing may be stepped or comprise a frustoconical transition between adjacent segments of different outer diameters.

The outer diameter of the probe housing may be dependent upon the intended use of the probe. It is generally desirable for the probe housing to have a narrow diameter to reduce the size of surgical incision that is required when using the probe. In some embodiments, the probe housing may have a maximum outer diameter of between about 3 mm and about 20 mm; typically between about 4 mm and about 15 mm or between about 6 mm and about 10 mm, depending on the intended use of the probe. A probe for use in laparoscopy or robotic surgery, for example, may have a diameter of between about 4 mm and about 6 mm.

Suitably, the probe housing may have a wall thickness of between about 0.2 mm and 3 mm; typically between about 0.5 mm and about 1 mm.

An air gap may be required between the at least two first coils and the at least one second coil and an internal surface of the probe housing to reduce thermal effects. The air gap may suitably be between about 0.2 mm and about 3 mm; typically between about 0.5 mm and about 1 mm in the radial dimension.

Suitably, at least some and preferably all of the coils as well as the baseline voltage taring device may be disposed within a head portion of the probe housing proximate a distal sensing end or tip of the probe. Preferably, at least one sensing coil is disposed as close as possible to the distal end to optimise the sensitivity of the probe, e.g. within about 5 mm of the distal end; preferably within about 3 mm of the distal end; more preferably within 2 mm from the distal end.

In some embodiments, the coils may be mounted on an elongate former or other support within the housing. Suitably the former or other support may be formed of an insulating material or comprise an insulating layer between the former or support and the coils.

Alternatively, in some embodiments at least one of the coils may be disposed outside of the probe housing. For example, at least one of the coils may wrap around and be supported by an outer surface of the probe housing.

The one or more drive coils are suitably connected to a selectively operable AC current source (not shown) that provides a drive current for operating the probe. In some embodiments, the probe may comprise more than one drive coil. In such case, the drive coils may be connected in series or anti-series as described herein and may be connected to the same current source. The one or more drive coils are excited by the drive current to produce the driving magnetic field. The strength of the driving magnetic field is dependent upon the number and configuration of the drive coils, the current passing through the one or more drive coils and the number of turns of the or each drive coil.

In use, the driving magnetic field induces a magnetic marker in the vicinity of the probe to generate a response field.

In some embodiments, the magnetic marker may be a ferromagnetic marker. Suitable exemplary markers are disclosed by WO2014013235A1, WO 2016/193753, WO2019180580A1, United Kingdom patent application no. 2115827.4 and United Kingdom patent application no. 2115826.6, the disclosure of each which is incorporated herein by reference.

The response field from the marker is dependent upon the strength of the driving magnetic field experienced by the marker, which in turn is dependent upon the proximity of the marker to the one or more drive coils. It will be understood that where there are two or more drive coils that are spaced axially along the probe, the driving magnetic field experienced by the marker may originate mainly from the drive coil(s) that are closer to the marker; typically those which are disposed closer to the distal end of the probe. The response field is also dependent upon the magnetic permeability of the marker.

The response field from a marker is detected by the one or more sense coils as a sense voltage. As with the drive coils, where the probe has more than one sense coil, the response field may be detected more strongly by the sense coil(s) that are disposed closer to the marker in use; typically those at or close to the distal tip of the probe. Where two or more sense coils are provided, one or more may be provided to sense a voltage across the sense coils that results directly from the driving magnetic field so that can be subtracted from the sense voltage, as described below. However, in the event that the tip of the probe is moved past a marker in use, the marker may respond more strongly to a driving magnetic field generated by a drive coil disposed further from the distal end, and the response field may be detected more strongly by a sense coil positioned further from the distal end.

The sense voltage across the one or more sense coils which results from the response field generated by the marker correlates to the distance between the probe and the marker and is suitably output to a signal processor (not shown) for calculating the proximity of the marker relative to the probe and for outputting a suitable dynamic audible, visible or other perceptible signal representing the proximity; e.g. a visible indication of distance in numbers on a display.

However, a voltage (referred to herein as a "baseline voltage") is also induced in the one or more sense coils by the driving magnetic field produced by the one or more drive coils. Both a magnetic marker and the one or more drive coils may increase or decrease the magnetic flux that passes through a sense coil. The closer a drive coil is positioned to a sense coil, and the stronger the driving magnetic field, the greater the baseline voltage. It will be appreciated by those skilled in the art that the baseline voltage is typically be much larger than the component of the sense voltage that results from the response field. When the probe is used to detect a marker, the baseline voltage induced in the one or more sense coils by the driving magnetic field should therefore be minimised, such that the sense voltage across the one or more sense coils is primarily results from the response field of the marker, thereby to allow the proximity of the marker to be accurately determined. A significant baseline voltage is undesirable, as it may obscure the sense voltage originating from the marker.

The baseline voltage can be reduced and potentially eliminated in several different ways. In some embodiments, the first or second coils may be configured or arranged to minimise the baseline voltage component of the sense voltage induced in the one or more sense coils that is attributable directly to the driving magnetic field. For example, the first coils may comprise two or more drive coils which are connected in anti-series or have opposite windings to produce a driving field of minimal, ideally zero, strength at the location of at least one sense coil as a second coil, so that the sense voltage across the sense coil results predominantly, ideally entirely, from the response field of the marker. This may require, for example, arranging the sense coil at a midpoint between two substantially identical drive coils.

Alternatively, the first coils may comprise at least two sense coils. One sense coil may be disposed proximate the distal end of the probe for detecting the marker, while another sense coil may be disposed remote from the distal tip. At least one driving coil may be provided as a second coil to generate a driving field in use. Typically, one or more drive coils may be interposed between the sense coils. Alternatively, one or more drive coils may be arranged proximate each sense coil to form two sets of coils; each set comprising a sense coil and at least one drive coil. For example, as described herein, a single drive coil may be positioned adjacent each sense coil, or each sense coil may be interposed between two adjacent drive coils. The two sense coils may be positioned symmetrically within the driving field, so that each sense coil experiences substantially the same driving field. The two sense coils may be sufficiently far apart that a marker positioned in the driving field only generates a significant sense voltage in one of them; usually the one proximate the probe tip. The sense voltage generated across the other sense coil may be subtracted from the sense voltage generated across the one sense coil so that the net sense voltage across the sense coils results predominantly from the response field. For example, the two sense coils may be connected in anti-series or have opposite winding directions so that the sense voltages induced across them have mutually opposing polarities.

In an alternative arrangement, the sense voltages from the two or more sense coils may be input separately to the signal processor, which may be configured in use to process the sense voltages to minimise the baseline voltage resulting from the driving field. Thus in some embodiments the baseline voltage across the one or more sense coils may be physically reduced by suitable configuring or arranging of the coils, while in other embodiments, the baseline voltage may be reduced by processing at the signal processor signals representing the voltages sensed by the sense coils.

In practice, it is difficult to eliminate the baseline voltage using only the arrangement of the at least one drive coil or sense coil, because of manufacturing tolerances of the probe and the coils. This may especially be the case for relatively narrow probes incorporating small diameter coils, e.g. probes having a diameter of less than about 15 mm, or even more especially less than about 10 mm. In accordance with the present disclosure, a baseline voltage taring device comprising a first conductor that defines an arcuate conducting path extending azimuthally around the probe axis juxtaposed, i.e. near or adjacent to or, more generally, in the vicinity of the one or more sense coils may be used to reduce further the baseline voltage. The first conductor is connected to a selectively operable current source such that in use it also generates a magnetic field in use, which is referred to herein as a balancing magnetic field. The conducting path extends partially (i.e. not fully) around the probe axis and is configured as disclosed herein to offset a residual baseline voltage across the one or more sense coil resulting directly from the one or more drive coils.

In some embodiments, the probe may comprise at least two sense coils that are axially separated along the probe axis, and a drive coil which is interposed between the at least two sense coils. In this case, at least two of the sense coils may be connected in anti-series or coiled in opposite directions, as described above. A voltage may be induced in each sense coil by the driving magnetic field. At least one of the sense coils may be coiled in the same direction as the at least one drive coil, and at least one of the sense coils may be coiled in the opposite direction to the at least one drive coil. In use, opposing voltages are thus induced in the sense coils that are coiled in opposite directions. In this embodiment, the baseline voltage is the sum of the voltages induced in the sense coils as a result of the driving field.

In some embodiments, the probe may comprise two sense coils and a single drive coil disposed between the two sense coils. One of the sense coils may be disposed proximate the distal end of the probe: the drive coil may be positioned proximally of the one sense coil: the other sense coil may be positioned proximally of the drive coil. Suitably, the distance between the two sense coils may be such that a marker disposed at or distally of the distal end of the probe does not give rise to any significant sense voltage in the other proximal sense coil. The drive coil may suitably have a length of between about 2 mm and about 10 mm. The drive coil may comprise between about 10 and about 150 turns of wire; typically between about 10 and about 60 turns. Each sense coil may have a length of between about 0.5 mm and about 6 mm. Each sense coil may comprise between about 50 and about 1000 turns of wire; typically between about 100 and about 500 turns. The two sense coils may comprise the same number of turns and be of approximately the same length. The separation between each coil may be between about 0.5 and about 1.0 mm.

For two sense coils that are coiled in anti-series but are otherwise identical, and a drive coil that is centred exactly on the midpoint between the two sense coils, when a driving current passes through the drive coil, in the absence of a magnetic marker, approximately equal and opposite voltages are induced in the two sense coils by the driving magnetic field, resulting in a net sense voltage of zero. In practice, the two sense coils may not be identical or the drive coil may not be centred exactly at the midpoint between the two sense coils owing to manufacturing tolerances. The voltages induced in the two sense coils may therefore be opposite but unequal, and there may be a net resulting baseline voltage.

A baseline voltage taring device may therefore be used in accordance with the present disclosure to reduce or, preferably, eliminate the net resulting baseline voltage. A driving current may pass through the first conductor along the conducting path to generate a balancing voltage that opposes and at least partially offsets the baseline voltage. The conducting path may suitably be positioned off-centre from the midpoint between two sense coils, proximate, or adjacent to one of the sense coils. If the conducting path is positioned off-centre from the midpoint between two sense coils, the passage of current in the conducting path may induce a voltage in both sense coils, but the magnitude of the voltage induced in one of the sense coils may be larger than the voltage induced in the other sense coil. The conducting path may be arranged proximate, or adjacent to one of the sense coils, and may be at a small axial separation from one of the sense coils. The conducting path may therefore induce an additional balancing voltage in one of the sense coils, reducing any difference in magnitude in the sense voltages induced in the two sense coils by the driving field, and thereby at least reducing the net baseline voltage, such that the sense voltage is at least predominantly attributable to the response field generated by the marker in response to the driving field.

As described above, in some embodiments, the probe may comprise at least two drive coils that are axially separated along the length of a probe and a sense coil disposed between the at least two drive coils. Suitably, one of the drive coils is positioned as close as possible to the distal end of the probe. In this case, at least two of the drive coils may be connected in anti-series or coiled in opposite directions.

In use, two similar drive coils connected in anti-series or wound oppositely generate opposing magnetic fields, leading to a null point at or close to the midpoint between the two drive coils and symmetrically opposing magnetic fields either side of the midpoint. A sense coil may be disposed between the two drive coils. The sense coil may have a length of between about 0.5 mm and about 6 mm. The sense coil may comprise between about 50 and about 1000 turns of wire; typically between about 100 and about 500 turns. Each drive coil may have a length of between about 0.75 and about 6 mm. Each drive coil may comprise between about 10 and about 150 turns of wire; typically between about 10 and 60 turns. The two drive coils may comprise the same number of turns and be of approximately the same length. The separation between each coil may be between about 0.5 and about 1.0 mm.

In use, each drive coil induces a voltage in the sense coil. Drive coils coiled in anti-series or wound oppositely induce opposing voltages in the sense coil. The net voltage induced in the sense coil is the baseline voltage. If the sense coil were to be positioned exactly at the midpoint between the drive coils, and if the drive coils were identical but connected in anti-series, the balancing voltage induced in the sense coil would be zero. In practice the drive coils may not be identical, and the sense coil may not be centred exactly at the midpoint between the drive coils; for example, owing to manufacturing tolerances. There may therefore be a small resulting baseline voltage.

The baseline voltage taring device may suitably be configured and arranged at least to reduce and preferably eliminate the baseline voltage. In use, a driving current is caused to pass through the conducting path, such that the conducting path generates a balancing magnetic field. The balancing magnetic field from the conducting path induces a balancing voltage in the sense coil. The conducting path is configured such that the balancing voltage substantially offsets the baseline voltage. In particular, the azimuthal length of the conducting path about the probe axis may be such that the balancing voltage substantially offsets the baseline voltage. The conducting path may suitably be located between two drive coils, off-centre from the midpoint between the two drive coils. The conducting path may be disposed proximate or adjacent to one of the coils.

In some embodiments, the probe may comprise a first set of coils comprising at least one drive coil and at least one sense coil, and a second set of coils comprising at least one drive coil and at least one sense coil. The first set of coils and the second set of coils may be axially separated along the length of the probe. Preferably one of the sets of coils is disposed proximate the distal end of the probe.

In some embodiments, the first set of coils may comprise a drive coil and a sense coil, and the second set of coils may comprise a drive coil and a sense coil. The first set of coils and the second set of coils may be substantially identical. Suitably, the two sense coils may be positioned in similar relation to their respective drive coils. Each sense coil may be positioned proximally or distally of its associated drive coil. In some embodiments, both sense coils may be disposed distally of their respective drive coils. In other embodiments, both sense coils may be disposed proximally of their respective drive coils. In yet other embodiments, one of the sense coils may be disposed distally of its drive coil and the other sense coil may be disposed proximally of its respective drive coil. Preferably, the one sense coil is disposed at or proximate the distal end of the probe. A suitable coil arrangement is disclosed by United Kingdom patent application no. 2204999.3 and International patent application no. PCT/GB2023/050909, the disclosure of each of which is incorporated herein by reference.

Suitably, each set of coils may comprise two substantially identical drive coils; i.e. the drive coils may have substantially the same dimensions as each other and may comprise the same number of turns of wire.

In some implementations, each drive coil may have an outer radius of between about 0.5 mm and 10 mm; typically between about 1.5 mm and about 6 mm. The radius of the drive coils may be selected to be appropriate for the diameter of the probe, for example as described above.

In some implementations, each drive coil may have an axial length of between about 0.2 mm and 10 mm; typically between about 0.5 mm and about 2.5 mm.

In some implementations, each drive coil may have between about 10 and about 150 turns of wire typically between about 10 and about 60 turns of wire.

The sense coil of each set of coils may have an axial length of between about 0.5 mm and 6 mm; typically between about 0.75 mm and about 2 mm.

The sense coil of each set of coils may have a mean radius of between about 0.5 mm and 10 mm; typically between about 1.5 mm and about 6.5 mm. Conveniently, the first sense coil may have a similar mean radius to the mean radius of the drive coils of the respective set of coils.

Typically, sense coil of each set of coils may comprise between about 50 and about 1000 turns of wire. In some implementations, the sense coil may have between about 100 and about 500 turns of wire.

Suitably, the sense coil of each set of coils may be formed from wire having a diameter of between about 0.01 and 0.3 mm; typically between about 0.025 mm and 0.1 mm.

In some implementations, the sense coil of each set of coils may comprise between about 3 and 20 superposed layers; typically between about 8 and 10 layers of turns; with each layer having between about 5 and 50 turns; typically between about 15 and about 20 turns.

As disclosed by United Kingdom patent application no. 2204999.3 and International patent application no. PCT/GB2023/050909, the distance between the centre of each sense coil and the centre of each drive coil within the same set of coils may advantageously be between about 1 mm and about 3 mm.

The total axial distance spanned by the first and second sets of coils may be between about 10 mm and 100 mm; typically between about 19 mm and about 30 mm. In some implementations, the axial separation between the sense coils of the first and second sets of coils may be between about 3 mm and about 100 mm; typically between about 12 mm and about 15 mm.

Suitably, the distance between the two sense coils is such that in use a marker disposed distally of the distal sense coil generates substantially no sense voltage in the distal sense coil, whereby the sense voltage in the proximal sense coil results almost entirely from the driving field and is substantially the same as a component of the sense voltage induced in the distal sense coil as a result of the driving field. As described above therefore, the sense voltage in one of the sense coils can be used to isolate the sense voltage in the other sense coil that results from the sense response of the marker. The sense coil of the first set of coils and the sense coil of the second set of coils may thus be connected in anti-series or have opposite winding directions. Meanwhile, the drive coil of the first set of coils and the drive coil of the second set of coils may suitably be connected in series.

The voltage induced in one of the sense coils by the respective drive coil may therefore be approximately equal and opposite to the voltage induced in the other sense coil by its respective drive coil. If the first set of coils is not identical to the second set of coils or if there is insufficient axial separation between the first set of coils and the second set of coils, the voltage induced in the second sense coil may not completely offset the voltage induced in the first sense coil, and a residual baseline voltage may result. The baseline voltage taring device may be configured to offset this residual baseline voltage. The conducting path defined by the baseline voltage taring device may thus be positioned between the first set of coils and the second set of coils. The conducting path may be positioned proximate, or adjacent to one of the first set of coils or the second set of coils. A driving current may pass through the conducting path, thereby generating a magnetic field. The magnetic field from the conducting path may generate a balancing voltage in one of the sense coils (or an unequal voltage in both of the sense coils). The azimuthal length of the conducting path is such that the balancing voltage from the conducting path induced in the sense coils substantially offsets any residual baseline voltage from the drive coils.

In some embodiments, the first set of coils may comprise a first sense coil disposed between a first pair of drive coils. The second set of coils may comprise a second sense coil disposed between a second pair of drive coils. Suitably, the first set of coils may be substantially identical to the second set of coils.

The first set of coils may comprise a substantially identical first pair of drive coils. The first pair of drive coils may be connected in series.

The second set of coils may be substantially identical to the first set of coils. The second set of coils may comprise a substantially identical second pair of drive coils. The second pair of drive coils may be substantially identical to the first pair of drive coils. The second pair of drive coils may be connected in series. The second pair of drive coils may be connected in series with the first pair of drive coils. Suitably, the first pair of drive coils and the second pair of drive coils may be connected to the same current source.

Suitably, one of the first and second sense coils may be connected with the same polarity as its respective pair of drive coils. The other of the second and first sense coils may be connected with the opposite polarity from its respective pair of drive coils. Thus, in some embodiments, the two pairs of drive coils may be connected in series with each other, with the same polarity as one of the sense coils, while the other sense coil is connected with the opposite polarity from the drive coils and the one sense coil. In some embodiments, the two sense coils may be connected in anti-series or connected in series but with opposing directions of winding. In an alternative arrangement, as described above, the sense coils may be adapted for connection separately to the signal processor so that the sense voltage induced in one of the sense coils by the driving magnetic field can be used in processing to strip out the component of the sense voltage in the other sense coil from the driving magnetic field, leaving only the sense voltage arising from the marker response field and any residual baseline voltage.

Advantageously, the first set of coils may be positioned proximate to the distal sensing end of the probe. When a driving current passes through the first set of drive coils, a driving magnetic field is generated. The driving magnetic field may induce a response field from a magnetic marker proximate to the distal end of the probe, which may be detected as an induced voltage in the first sense coil. A voltage is also induced in the first sense coil from at least the first pair of drive coils. Those skilled in the art will appreciate that that the sense voltage resulting from the driving field is typically much larger than the sense voltage from the response field.

A driving field passing through the second pair of drive coils generates a driving magnetic field and induces a voltage in the second sense coil. When the second sense coil is coiled in anti-series with the first sense coil and the second pair of drive coils is substantially the same as the first pair of drive coils, the voltage induced in the second sense coil from the second pair of drive coils is ideally equal and opposite to the voltage induced in the first sense coil from the first pair of drive coils. The net voltage induced in the sense coils from the drive coils, which is the baseline voltage, may therefore be zero or close to zero, allowing any sense response from the marker to be detected.

In practice, the first pair of drive coils are unlikely to be identical to the second pair of drive coils, the first sense coil is unlikely to be identical to the second sense coil, and the first and second sense coils are unlikely to be situated at the exact midpoint between the drive coils, for example, owing to manufacturing tolerances. As a result, the baseline voltage is unlikely to be exactly zero. This is especially true in small diameter probes (e.g. less than about 15 mm, especially less than about 10 mm) where the magnetic fields in and around the coils are higher than in wider probes, as their dimensions are smaller. Small changes in positioning or drive current therefore generally result in larger changes in drive field, and therefore also in sensed voltage. This may obscure or interfere with measurements of a sense voltage induced from a marker.

The conducting path of the baseline voltage taring device may be configured in accordance with the present disclosure further to reduce or even substantially eliminate the baseline voltage. The conducting path provided by the first conductor may suitably be disposed between the first set of coils and the second set of coils. The conducting path may be provided at a fixed axial position between the first set of coils and the second set of coils. The conducting path may be disposed off-centre from the midpoint between the first set of coils and the second set of coils. The conducting path may therefore be positioned closer to one of the first and second sense coils. Conveniently, the conducting path may be connected to the same current source as the first or second set of drive coils. When a current passes through the conducting path, a balancing magnetic field is generated, which induces an additional balancing voltage in the first or second sense coil. The voltage induced may be larger in the first sense coil or the second sense coil. The conducting path may be configured such that the balancing voltage induced by current passing through the conducting path opposes the baseline voltage.

As described disclosed herein, the conducting path is formed by the first conductor. Generally, the first conductor may be disposed intermediate two drive coils or two sense coils to produce the balancing voltage in the one or more sense coils. The conducting path defined by the first conductor should be positioned off-centre between the two drive coils or two sense coils in the direction of the probe axis. The first conductor may be connected to a suitable current source in any convenient manner known to those skilled in the art. Conveniently, the first conductor may be connected to the same current source as the at least one drive coil. Typically, the first conductor is connected to the current source at two spaced locations on the first conductor, thereby defining the conducting path intermediate the two locations. The balancing voltage afforded by the baseline voltage taring device is a function of the azimuthal length of the conducting path between the two locations.

In some implementations, the baseline voltage taring device may conveniently comprise a second elongate conductor which extends around the probe and at least one conducting bridge extending in an axial direction to interconnect the first and second conductors. The conducting bridge therefore determines the azimuthal length of the conducting path on the first conductor intermediate the conducting bridge. The second conductor may also define a conductive path around the probe axis juxtaposed the conductive path defined by the first conductor. In some implementations, the conductive path defined by the second conductor may be aligned with the midpoint between the two sense coils or two drive coils so it does not contribute to the balancing voltage for convenience. In some embodiments, however, the conductive path of the second conductor may also be disposed off-centre so that it contributes to the balancing field.

One or both of the first and second conductors may extend fully or partially around the probe. In some embodiments, therefore, one or both of the first and second conductors may form complete loops. Alternatively, one or both of the first and second conductors may form an arc which extends partially but not completely around the probe axis. In some implementations, one or both of the first and second conductors may extend azimuthally around the probe axis in a plane perpendicular to the probe axis. In some embodiments, the first and second conductors may be substantially parallel to each other.

Suitably, one or both of the first and second conductors may comprise a conductive wire or strip; e.g. a copper wire or strip. Thus, in some implementations, the first or second conductor may comprise a loop of copper wire. A suitable conductive strip may comprise an flexible insulating film which is coated with a thin layer of conductive material. A suitable insulating film is polyimide film, which is commercially available from E. I. du Pont de Nemours and Company, Wilmington, Delaware, USA under the trade mark Kapton®. A suitable conductive material is copper.

Suitably, each of the first and second conductors is connected to the current source and the at least one conducting bridge connects the first and second conductors together to complete a circuit. In some implementations, the at least one conducting bridge may extend between the first and second conductors in a direction that is substantially perpendicular to at least one of the first and second conductors. Suitably, the at least one conducting bridge may comprise a conducting wire or strip. The materials described above for the first and second conductors may also be suitable for the conductive bridge In some embodiments, the at least one conducting bridge may be moveable between a plurality of azimuthal positions around the probe axis. A single conducting bridge may extend between the first and second conductors and may be moveable by sliding between a plurality of azimuthal positions. The conducting bridge may be moveable in discrete steps between a plurality of azimuthal positions.

In some embodiments, one or both of the first and second conductors may comprise a plurality of conductive lands at a series of azimuthally spaced positions around the probe axis. The lands on the or each conductor may extend in a direction substantially parallel to the probe axis towards the other conductor. Each land on one conductor suitably terminates short of the other conductor, thereby defining a short gap therebetween. The conducting bridge may comprise a conductive strip that is adapted to form a connection across the gap between a land on one of the conductors and the other conductor at a selected azimuthal position around the probe axis. By moving the conducting bridge between a plurality of azimuthal positions, the azimuthal length of the conducting path may be adjusted for controlling the magnitude of the balancing magnetic field, thereby to minimise the baseline voltage across the one or more sense coils. Alternatively, the conducting bridge may be provided between the first and second conductors at a fixed azimuthal position. Advantageously, the fixed azimuthal position of the conductive bridge may be selected such that the azimuthal length of the conducting path defined by the first conductor is optimised to offset at least partially the baseline voltage.

In some embodiments, the baseline voltage taring device may comprise a flexible circuit board that is wrapped at least partially around the probe axis. Suitably, the circuit board may be a printed circuit board. The circuit board may comprise two conducting traces which define the first and second conductors and a plurality of conducting lands extending from one or both of the first and second conductors at a series of azimuthally spaced positions as described above. One or more conducting bridges may be provided to extend between a land on one of the conductors and the other conductor, thereby to define the azimuthal length of the conducting path. The one or more conducting bridges may, for example, be formed of a suitable conductive tape which is affixed across a gap between the land on the one conductor and the other conductor, or a conducting bridge may be formed by soldering between the land on the one conductor and the other conductor. Other methods of interconnecting a land on one of the conductors and the other conductor will be apparent to those skilled in the art.

According to a second aspect, the present disclosure provides a method of manufacturing a probe for sensing a magnetic marker during a surgical procedure, the method comprising;

mounting at least two first coils and at least one second coil substantially coaxially on a longitudinal axis of the probe, the at least two first coils being one of sense coils or drive coils and the at least one second coil being the other of a drive coil or sense coil, such that the one or more drive coils are connectable to a current source to generate a driving magnetic field through the one or more drive coils, and the one or more sense coils are connectable to a signal processor for processing one or more sense voltages induced in the respective one or more sense coils to generate an output signal; the first or second coils being configured or arranged to minimise a baseline voltage component of the sense voltage induced in the one or more sense coils that is attributable directly to the driving magnetic field or to output to the signal processor separate sense voltages from two or more sense coils to allow the signal processor to process the sense voltages to minimise a baseline voltage component of the sense voltages that is attributable directly to the driving magnetic field; whereby the first and second coils are configured and arranged as a gradiometer for measuring the proximity of a magnetic marker to the probe and the output signal represents the distance between the marker and the probe; and fitting to the probe a baseline voltage taring device comprising a first elongate conductor such that the first conductor defines a conducting path extending partially around the probe axis, and is connectable to a current source to generate a balancing magnetic field in the vicinity of the one or more sense coils, such that in use the balancing magnetic field induces a balancing voltage in the one or more sense coils which at least partially offsets the baseline voltage; whereby the sense voltage is at least predominantly attributable to a response field generated by the marker in response to the driving field, which corresponds to the proximity of the marker.

The probe may be a probe comprising any of the features disclosed above. Thus, the conducting path may extend partially around the probe axis juxtaposed the one or more sense coils. The conducting path may typically be fitted to the probe in off-centre or asymmetrically with respect to the arrangement of the at least two first coils and at least one second coil.

Suitably, the method may further comprise adjusting the azimuthal length of the conducting path around the probe to minimise the baseline voltage across the one or more sense coils.

Adjusting the azimuthal length of the conducting path may comprise moving a conducting bridge of the kind described above to an azimuthal position around the circumference of the probe such that the baseline voltage is minimised. A plurality of conductive lands or tabs may extend partway between the first conductor and a second conductor at different azimuthal positions. Adjusting the length of the conducting path may comprise completing a connection between at least two corresponding lands or tabs, thereby forming a conducting bridge. The connection may suitably be completed by soldering a connector between the conductors.

According to a third aspect, the present disclosure provides a method of setting up a probe for sensing a magnetic marker for use in surgery, the probe comprising:

at least two first coils and at least one second coil which are arranged substantially coaxially on a longitudinal axis of the probe as a gradiometer for measuring the proximity of a magnetic marker to the probe; the at least two first coils being one of either sense coils or drive coils the at least one second coil being the other of a drive coil or sense coil; the one or more drive coils being adapted for connection to a current source to generate a driving magnetic field, and the one or more sense coils being adapted for connection to a signal processor for processing a sense voltage induced in the one or more sense coils to generate an output signal; the first or second coils being configured or arranged to minimise a baseline voltage component of the sense voltage induced in the one or more sense coils that is attributable directly to the driving magnetic field or to output to the signal processor separate sense voltages from two or more sense coils to allow the signal processor to process the sense voltages to minimise a baseline voltage component of the sense voltages that is attributable directly to the driving magnetic field;

a baseline voltage taring device comprising a first elongate conductor which defines a conducting path extending partially around the probe axis juxtaposed the one or more sense coils and is connectable to a current source to generate a balancing magnetic field in the vicinity of the one or more sense coils;

the method comprising adjusting an azimuthal length of the conducting path around the probe axis to control the balancing magnetic field to induce a balancing voltage across the one or more sense coils which at least partially offsets the baseline voltage.

The probe may include any of the features disclosed above.

It will be understood that method comprises effectively tuning the balancing magnetic field by varying a azimuthal length of the conducting path around the probe axis, such that the balancing voltage minimises the baseline voltage.

Varying the azimuthal length of the conducting path around the probe axis may comprise moving the conducting bridge to an azimuthal position around the probe axis such that the baseline voltage is minimised. Varying the azimuthal length of the conducting path around the probe axis may comprise completing a connection between at least two conductors, thereby forming a conducting bridge. A plurality of conducting strips may extend partway between the at least two conductors at different azimuthal positions, and the connection may be completed by soldering a conducting connection between a selected copper strip and the at least two conductors.

The method of setting up the probe of the present disclosure may be carried out as part of the manufacture of the probe. In some embodiments, the position of the conducting bridge may be adjustable to allow the probe to be recalibrated periodically or as required.

According to a fourth aspect, the present disclosure provides a detection apparatus for locating a magnetic marker during surgery, the apparatus comprising a probe according to the first aspect of the present disclosure, as described above, a current source which is selectively operable to generate a driving magnetic field through the one or more drive coils and the first conductor; and at least one signal processor which is configured to receive one or more sense voltages from the one or more sense coils and generate an output signal representing the distance between the probe and a magnetic marker.

In some embodiment, the apparatus may further comprise at least one implantable magnetic marker. Suitably, the magnetic marker may comprise a ferromagnetic marker; e.g. a Magseed® marker which is commercially available from Endomagnetics Ltd, Cambridge, UK.

Figure 3:
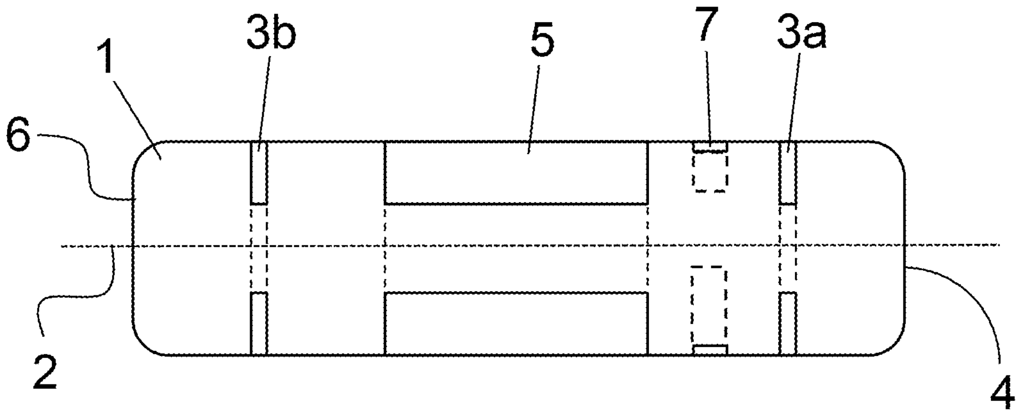
FIG. 3 is schematic longitudinal section through a mandrel for a probe according to an embodiment of the present disclosure, the mandrel carrying a long drive coil disposed between two sense coils and a taring device proximate to one of the sense coils.

FIG. 3 is a schematic longitudinal sectional view of part of a probe according to an embodiment of the present disclosure. In particular, FIG. 3 shows a generally cylindrical mandrel 1 which is shaped and dimensioned to be received within a correspondingly shaped recess in a probe housing (not shown) to a close tolerance, with a small air gap (e.g. about 1 mm) between an outer surface of the mandrel 1 and an inner surface of the housing. The mandrel 1 is suitably adapted to be fixedly secured to a distal end of hand-held wand as shown, for example in FIG. 1, such that the mandrel 1 is mounted at the distal end of the probe.

The mandrel 1 defines a longitudinal axis 2, which is aligned with a longitudinal axis of the probe, and carries two sense coils 3*a*, 3*b* which are axially separated along the probe axis 2. One of the sense coils 3*a* is disposed juxtaposed a distal end 4 of the mandrel 1 which is positioned at a distal sensing end (also referred to herein as the tip) of the probe when fitted. The other sense coil 3*b* is disposed juxtaposed a proximal end 6 of the mandrel 1. A long drive coil 5 is interposed between the sense coils 3*a*, 3*b*, approximately at a midpoint between the two sense coils. The sense coils 3*a*, 3*b* are connected in anti-series, so that sense voltages induced in them by a magnetic field have opposite polarities. Alternatively, the sense coils 3*a*, 3*b* may be wound in opposite directions from each other and connected in series to achieve the same effect. The long drive coil 5 is connected to a suitable current source (not shown), which may be housed in a base station of the kind shown in FIG.

1, to which the probe may be connected via a suitable cable. When a current passes through the drive coil 5, a driving magnetic field is generated.

The sense coils 3*a*, 3*b* are arranged for connection to a signal processor (not shown) which may also be housed for example in the base station. When the probe is in use, the driving magnetic field from the long drive coil 5 generates a response field from a magnetic marker (also not shown) in the vicinity of the probe; usually close to the distal end of the probe. The response field is detected by the signal processor as a sensing voltage in the sense coil 3*a* closest to the probe tip. A voltage is also induced in both distal and proximal sense coils 3*a*, 3*b* from the drive coil 5. As the sense coils 3*a*, 3*b* are connected in anti-series substantially equidistant from the drive coil 5, the drive coil 5 induces approximately equal and opposite voltages in the sense coils 3*a*, 3*b*. A net baseline voltage in the sense coils 3*a*, 3*b* resulting from the drive coil 5 is therefore close to zero. However, owing to manufacturing tolerances (for example, the sense coils 3*a*, 3*b* are unlikely to be identical, and the drive coil is unlikely to be positioned exactly centrally between the two sense coils 3*a*, 3*b*) the net baseline voltage induced in the sense coils 3*a*, 3*b* from the drive coil 5 is not exactly zero.

A baseline voltage taring device comprising a conductor 7 formed from an arcuate, elongate strip of conducting material is mounted to the mandrel 1 proximal the distal sense coil 3*a*. The conductor 7 is connected to the current source at circumferentially spaced terminals (not shown) and defines a conducting path between the connections which extends circumferentially partially around the mandrel 1. As shown in FIG. 3, the conductor 7 thus forms a conducting path which extends azimuthally around the probe axis 2, but does not form a complete loop.

When a current passes through the conducting path, the conducting path generates a balancing magnetic field that induces a balancing voltage in the sense coil 3*a*. The azimuthal length of the conducting path is such that the balancing voltage induced in the sense coil 3*a* reduces the baseline voltage from the drive coil 5. Advantageously, this means that sense voltage detected in the sense coil 3*a* is predominantly attributable to a marker. The sense voltage can therefore be processed by the signal processor to calculate the proximity of the marker to the probe and to generate an output signal representing the proximity. The output signal may be a display signal for displaying the distance between the marker and the probe on a suitable display, an audio signal having one or more parameters which vary according to the proximity and/or a haptic signal for generating a haptic response in the probe or another device in contact with a user which is indicative of the distance between the probe and the marker.

Figure 4:
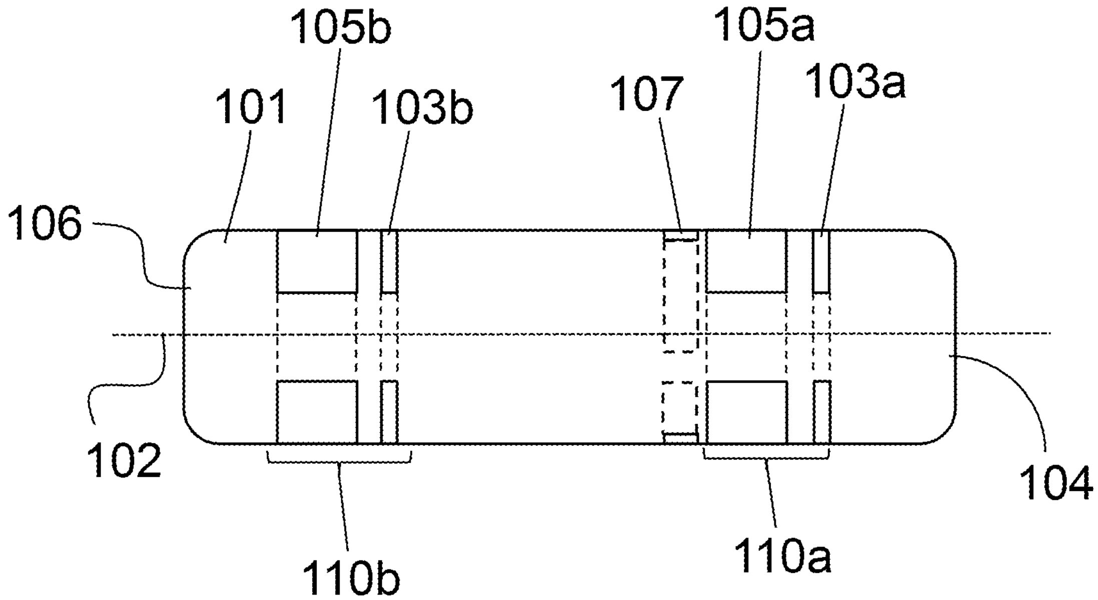
FIG. 4 is schematic longitudinal section through a mandrel for a probe according to a different embodiment of the present disclosure, the mandrel carrying two sets of coils; each set comprising a drive coil and a sense coil; and a taring device proximate to the first set of coils.

FIG. 4 is a schematic longitudinal section taken through a mandrel 101 forming part of a probe according to another embodiment of the present disclosure. The mandrel 101 is generally configured and arranged similarly to the mandrel 1 of FIG. 3 and is adapted to be fixedly secured to a distal end of hand-held wand, such that the mandrel 1 is mounted at the distal end of the probe. The wand is suitably configured for connection to a base station as shown in FIG. 1. The mandrel 101 supports a first pair of coils 110*a* adjacent a distal end 104 of the mandrel 101 and a second pair of coils 110*b* adjacent a proximal end 106 of the mandrel 101, which first and second pairs of coils 110*a*, 110*b* are axially separated along the axis 102 of the probe. The first pair of coils 110*a* comprises a first drive coil 105*a* and a first sense coil 103*a*: the second pair of coils 110*b* comprises a second drive coil 105*b* and second sense coil 103*b*. The second drive coil 105*b* and second sense coil 103*b* substantially identical to the first drive coil 105*a* and first sense coil 103*a* respectively. The first drive coil 105*a* and second drive coil 105*b* are connected to a current source (not shown) which may be housed in the base station and are connected in series. The first sense coil 103*a* and the second sense coil 103*b* are connected in anti-series and are arranged for connection to a suitable signal processor as described above. In an alternative arrangement, as described above in relation to FIG. 3, the first and second sense coils 103*a*, 103*b* may be connected in series but wound in opposite directions.

When a current is caused to pass through the first drive coil 105*a* and the second drive coil 105*b* in use, a driving magnetic field is generated. As a result, a voltage is induced in the first sense coil 103*a*, predominantly from the first drive coil 105*a*, and a voltage is induced in the second sense coil 103*b*, predominantly from the second drive coil 105*b*. As the sense coils 103*a*, 103*b* are connected in anti-series, the voltages induced in the sense coils 103*a*, 103*b* from their associated drive coils 105*a*, 105*b* are approximately equal and opposite. However, owing to manufacturing tolerances, the first drive coil 105*a* is unlikely to be identical to the second drive coil 105*b*, the first sense coil 103*a* is unlikely to be identical to the second sense coil 103*b*, and the spacing between the coils 103*a*, 105*a* of the first pair of coils 110*a* is unlikely to be equal to the spacing between the coils 103*b*, 105*b* of the second pair of coils 110*b*. As a result, the net baseline voltage summed from the two sense coils 103*a*, 103*b* is unlikely to be zero.

A baseline voltage taring device comprising a conductor 107 formed from an arcuate, elongate strip of conducting material which defines a circumferentially extending conducting path proximate the first drive coil 105*a*, between spaced terminals (not shown) on the conductor 107, is also mounted to the mandrel 201 and connected to the current source to generate a balancing magnetic field as described above. The conducting path extends around the probe axis 102 and has an azimuthal length between the terminals such that the balancing magnetic field induces a balancing voltage in the first sense coil 103*a* that at least partially offsets the baseline voltage. Advantageously, this means that voltage detected in the sense coil 103*a* will be at least predominantly attributable to a marker proximate to the probe, allowing the signal processor to determine the distance between the marker and the probe.

Figure 5:
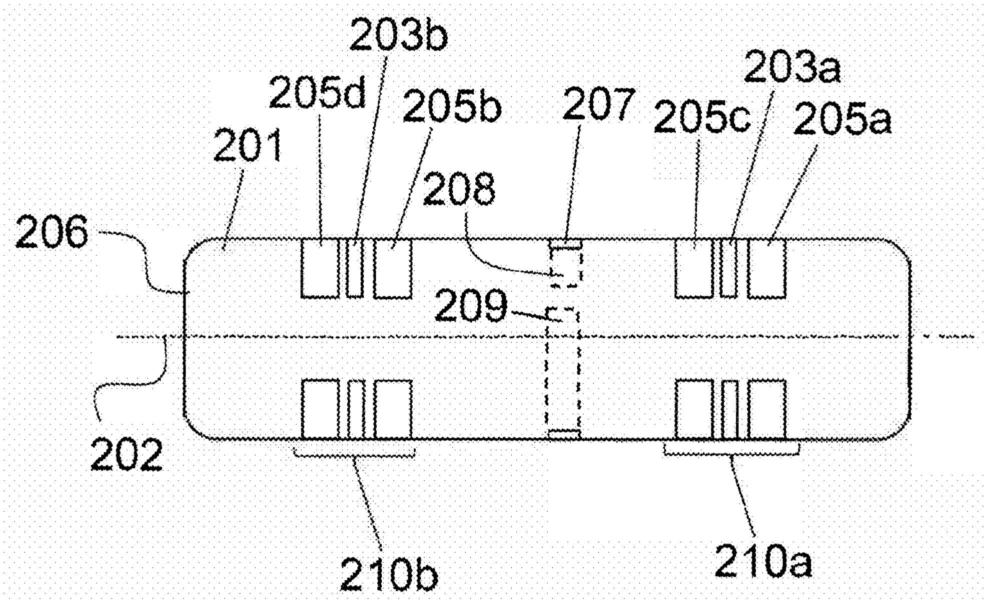
FIG. 5 is schematic longitudinal section through a mandrel for a probe according to another embodiment of the present disclosure, the mandrel comprising two sets of coils; each set comprising a pair of drive coils and a sense coil interposed therebetween; and a taring device disposed between the sets of coils.

FIG. 5 is a schematic longitudinal section taken through a mandrel 201 of a probe according to yet another embodiment of the present disclosure. The mandrel 201 is similar to the mandrels 1 and 101 of the first and second embodiments described above and is adapted to be fixedly secured to a distal end of hand-held wand, such that the mandrel 201 is mounted at the distal end of the probe. The mandrel 201 supports a first distal set of coils 210*a* and a second proximal set of coils 210*b* which are axially separated along a longitudinal axis 202 of the mandrel 201. The first set of coils 210*a* comprises a first pair of drive coils 205*a*, 205*c* and a first sense coil 203*a* interposed between the drive coils 205*a*, 205*c* of the first pair: the second set of coils 210*b* comprises a second pair of drive coils 205*b*, 205*d*, which is substantially identical to the first pair of drive coils 205*a*, 205*c*, and second sense coil 203*b*. The first pair of drive coils 205*a*, 205*c* and the second pair of drive coils 205*b*, 205*d* are connected in series to a current source (not shown) which may be housed in a suitable base station, as shown in FIG. 1. The first sense coil 203*a* and the second sense coil 203*b* are connected in anti-series with each other and are arranged for connection to a signal processor as described above. In an alternative arrangement, as described above in relation to FIGS. 3 and 4, the first and second sense coils 203*a*, 203*b* may be connected in series but wound in opposite directions.

When a current passes through the first pair of drive coils 205*a*, 205*c* and the second pair of drive coils 205*b*, 205*d* in use, a driving magnetic field is generated. The axial separation of the two sets of coils 210*a*, 210*b* is such that a voltage induced in the first sense coil 203*a* arises predominantly from the first pair of drive coils 205*a*, 205*c* and a voltage induced in the second sense coil 203*b* arises predominantly from the second drive coil 205*b*, 205*d*. As the sense coils 203*a*, 203*b* are connected in anti-series, the voltages induced in the sense coils 203*a*, 203*b* from their respective pairs of drive coils 205*a*, 205*c*; 205*b*, 205*d* are approximately equal and opposite to each other. However, owing to manufacturing tolerances, the first pair of drive coils 205*a*, 205*c* is unlikely to be identical to the second pair of drive coils 205*b*, 205*d*, the first sense coil 203*a* is unlikely to be identical to the second sense coil 203*b*, and the spacing between the coils in the first set of coils 210*a* is unlikely to be equal to the spacing between the coils in the second set of coils 210*b*. As a result, the net baseline voltage across the two sense coils 203*a*, 203*b* is unlikely to be precisely zero.

A baseline voltage taring device comprising an arcuate conductor 207 formed from an arcuate, elongate strip of conducting material is mounted to the outer surface of the mandrel 201 and defines a circumferentially extending conducting path between spaced terminals (not shown) on the conductor 207, intermediate the first set of coils 210*a* and the second set of coils 210*b*. The conductor 207 is conveniently connected to the current source via the terminals, which are suitably disposed at or proximate respective circumferential ends 208, 209 of the conductor 207, to generate a balancing magnetic field in use. It will be understood that in some embodiments, a separate current source for the conducting path may be provided if desired. The conductor 207 is located closer to one of the sets of coils 210*a*, 210*b* than the other 210*b*, 210*a* such that, in operation, it generates a magnetic field which induces a greater voltage across the sense coil 203*a*, 203*b* of the one set of coils 210*a*, 210*b*. The conductor 207 is configured such that the azimuthal length of the conducting path intermediate the terminals 208, 209 results in a net balancing voltage across the sense coils 203*a*, 203*b* that at least partially offsets the baseline voltage. Advantageously, this means that voltage detected in the sense coils 203*a*, 203*b* is predominantly attributable to a magnetic marker proximate the probe, allowing the signal processor to determine the distance between the marker and the probe. In an alternative arrangement, the conductor 207 may be replaced by a baseline voltage taring device of one of the kinds described below with reference to FIG. 6(*a*) and FIG. 6(*b*) or FIG. 7.

Figure 6A:
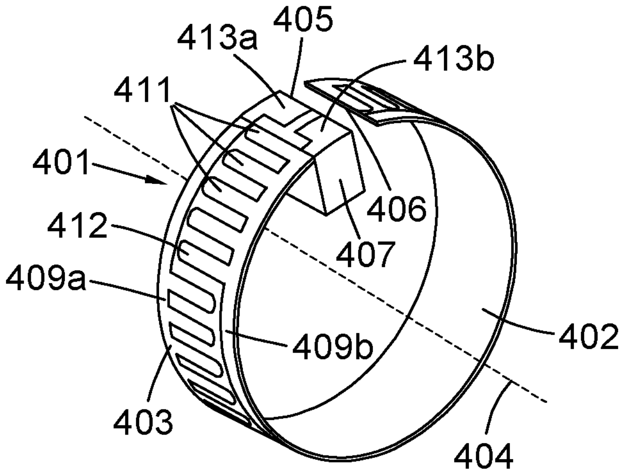
FIG. 6(*a*) is a perspective view of a taring device comprising a printed circuit board for use in a probe according to another embodiment of the present disclosure.
Figure 6B:
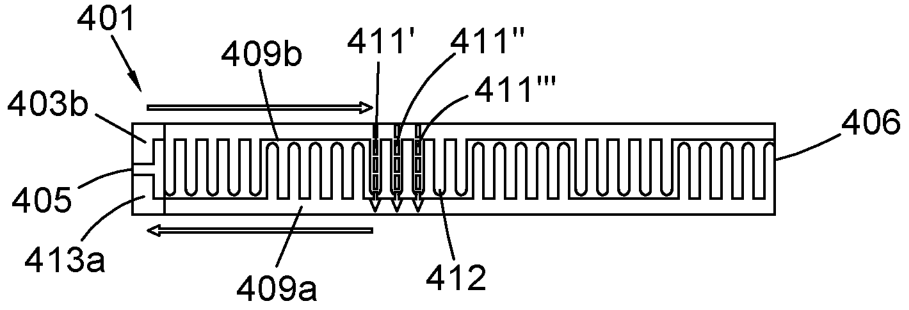

FIG. 6(*a*) is a perspective view of a baseline voltage taring device 401 according to another embodiment of the present disclosure: FIG. 6(*b*) is a plan view of the baseline voltage taring device 401 in an unrolled configuration for ease of reference. The taring device 401 is formed of a flexible printed circuit board comprising an insulating backing layer 402 and a conducting layer 403. Suitably, the conductive layer 403 may comprise a thin film of copper in the manner well known to those skilled in the art. The backing layer 402 may comprise any suitable insulating material which is flexible enough to be wrapped around and fixed to a cylindrical mandrel 1; 101; 201 similar to the ones described above. Alternatively, the backing layer 402 may comprise an insulating tape, such for example as a polyimide tape (e.g. Kapton® tape mentioned above).

The taring device 401 forms an incomplete loop as shown in FIG. 6(*a*) having two circumferential ends 405, 406 and defining a central axis 404 which aligns with the longitudinal axis 2; 102; 202 of the mandrel 1; 101; 201 when fitted. A tab 407 is attached to one of the circumferential ends 405 which is configured to be received in a corresponding recess (not shown) formed in the mandrel for locating the device 401 relative to the mandrel.

The copper layer 403 is etched in a manner known to those skilled in the art to form first and second axially spaced elongate conductors 409*a*, 409*b* which extend, one substantially parallel to the other, circumferentially around the device 401. Each conductor 409*a*, 409*b* comprises a plurality of circumferentially spaced lands 411 in the manner of rungs, which extend in a direction substantially parallel to the axis 404 of the device 401 between the conductors 409*a*, 409*b* at a series of different azimuthal positions and terminate in free ends 412 proximate the other conductor 409*b*, 409*a*. Each conductor 409*a*, 409*b* is formed with a terminal 413*a*, 413*b* juxtaposed the tab 407 for connecting the taring device 401 to a current source.

The balancing magnetic field to be generated by the taring device 401 in use can be tuned by selecting a land (e.g. 411', 411" or 411''') on one of the conductors 409*b*, 409*a* and making an electrical connection (not shown) between the selected land 411'; 411"; 411''' and the other conductor 409*a*, 409*b* to bridge across a short gap between the free end 412 of the land 411'; 411"; 411''' and the other conductor 409*a*, 409*b*. The electrical connection may be made, for example, by soldering across from the free end 412 to the other conductor, thereby forming a continuous electrical path, as indicated by the arrows in FIG. 6(*b*). Selection of the given land 411'; 411"; 411''' determines the azimuthal length of a conducting path defined by the conductors 409*a*, 409*b*. As disclosed herein, the azimuthal length of the conducting path determines the strength of the balancing magnetic field and therefore the balancing voltage induced in one or more sense coils from the taring device 401. The lands 411 which extend axially when fitted to the mandrel 1; 101; 201 do not contribute to the balancing field. Conveniently, the taring device 401 is fitted on the mandrel 1; 101; 201 such that one of the first and second conductors 409*a*, 409*b* is positioned midway between two sense coils 3*a*, 3*b*; 103*a*, 103*b*; 203*a*, 203*b* such that the field generated by that conductor affects the two sense coils substantially equally. In such case the balancing field is governed by the axial position and of the other conductor 409*b*, 409*a* and the azimuthal length of the other conductor between the terminal 413*b*, 413*a* and the selected land 411'; 411"; 411'''.

Figure 7:
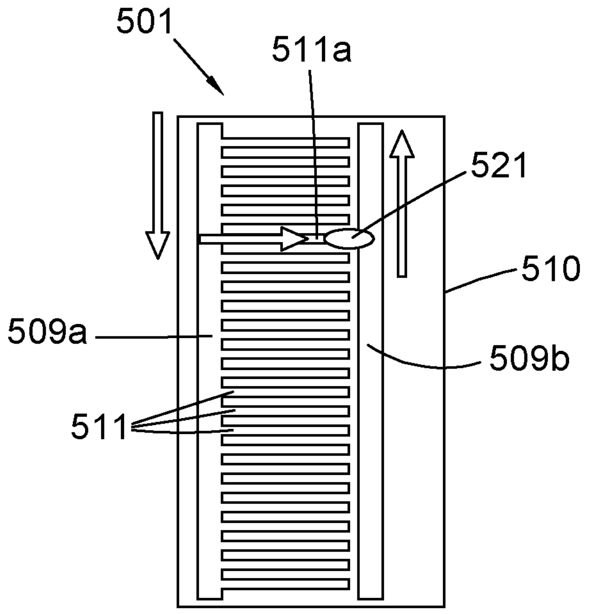
FIG. 7 is a schematic plan view of a different taring device comprising a printed circuit board, according to yet another embodiment of the present disclosure.

FIG. 7 is a plan view of a balancing voltage taring device 501 according to another embodiment of the present disclosure in an un-coiled configuration. The taring device 501 comprises a flexible printed circuit board 510. The circuit board 510 is etched with two elongate copper traces 509*a*, 509*b* which form first and second parallel conductors and a plurality of spaced copper lands 511 which extend part way between the traces 509*a*, 509*b*. In this embodiment, all of the lands 511 are connected to one of the traces 509*a*. A complete conducting path can be made by wiring or soldering a connection between a selected one of the copper rungs 511*a* and the other trace 509*b*, as shown at 521, thereby allowing current to flow around the path, as indicated by the arrows. In use the taring device 501 is capable of inducing a balancing voltage in one or more sense coils as disclosed here depending on the azimuthal length of the conducting path defined by the traces 509*a*, 509*b* and the location of the traces 509*a*, 509*b* relative to the one or more sense coils.

Figure 8A:
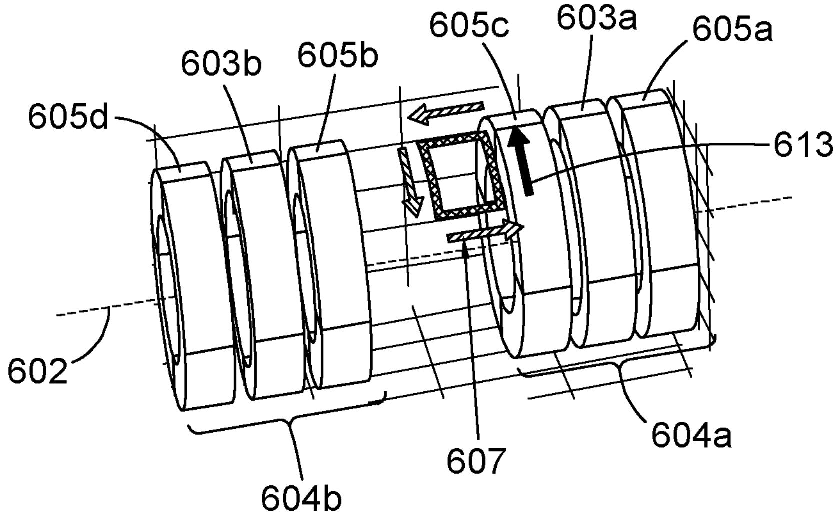
FIG. 8(*a*) is a perspective view of a coil arrangement of a probe according to another embodiment of the present disclosure, showing schematically a taring device that extends azimuthally partially around a longitudinal axis of the probe.
Figures 8B, 8C, 8D:
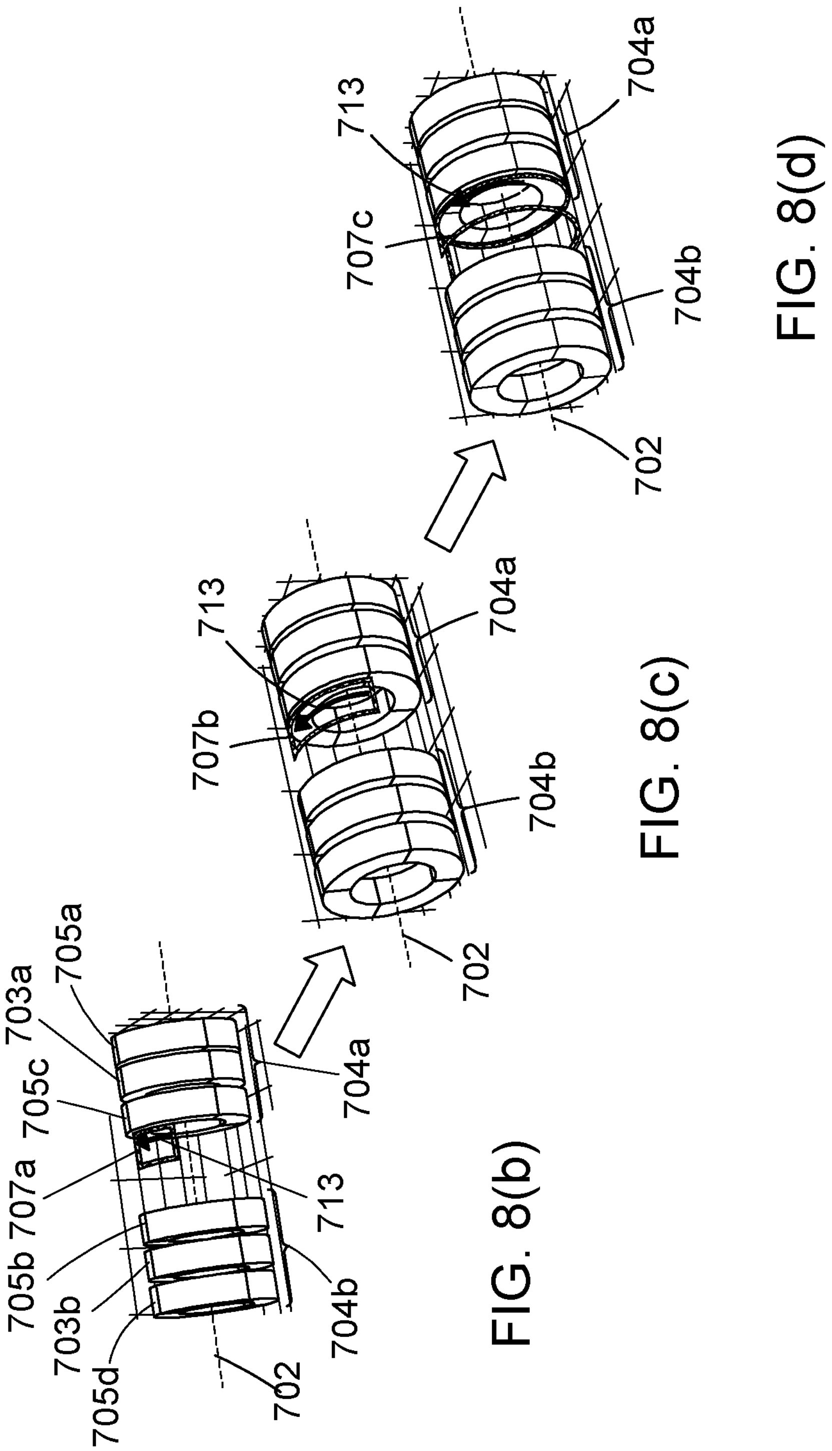

FIG. 8(*a*) is a schematic diagram of an arrangement of two sets of coils 604*a*, 604*b* forming a gradiometer for a susceptibility probe (not shown) according to another embodiment of the present disclosure, which illustrates how a conducting path 607 provided by a balancing voltage taring device of the kind described herein, which is interposed between the sets of coils 604*a*, 604*b*, provides a balancing magnetic field to induce a balancing voltage across two sense coils 603*a*, 603*b* of the two sets of coils for reducing a baseline voltage in the sense coils resulting from a driving magnetic field generated by drive coils of the sets of coils, whereby a sense voltage across the sense coils is predominantly attributed to a response field from a magnetic marker present in the driving field.

The arrangement comprises a first set of coils 604*a* and a second set of coils 604*b* arranged coaxially on a longitudinal probe axis 602; each set of coils comprising two spaced drive coils 605*a*, 605*c*; 605*b*, 605*d* and a sense coil 603*a*; 603*b* interposed between the drive coils 605*a*, 605*c*; 605*b*, 605*d*. The coils may be supported on a suitable coaxial former or mandrel (not shown) of the kind described above and housed within a probe housing (also not shown), with the first set of coils 604*a* positioned proximate a distal tip of the probe for maximal sensitivity.

The drive coils 605*a*, 605*b*; 605*c*, 605*d* are connected to each other in series and are suitably adapted for connection to an AC current source (not shown), such that they generate a driving magnetic field in use. The sense coils 603*a*, 603*b* of the two sets of coils are connected in anti-series and are arranged for connection to a signal processor, for example housed within a base station as shown in FIG. 1, for processing a sense voltage induced in the sense coils to calculate the distance between the probe and the magnetic marker. In an alternative arrangement, the sense coils 603*a*, 603*b* may be connected in series but coiled in opposite directions.

In use, the drive coils 605*a*, 605*b*, 605*c*, 605*d* generate approximately equal and opposite voltages in the two sense coils 603*a*, 603*b*, but owing to manufacturing tolerances, the net baseline voltage (i.e. the net voltage across the sense coils 603*a*, 603*b*) is unlikely to be exactly zero. This is especially true, as described above, for narrow probes (e.g. less than about 10 mm) with small coil diameters.

As disclosed herein, the conducting path 607 is provided in an off-centre position between the first set of coils 604*a* and the second set of coils 604*b* in a direction parallel to the probe axis 602. In FIG. 8(*a*), the conducting path 607 is shown as a complete circuit for illustrative purposes, but in practice includes terminals for connecting to a current source for driving current through the conductive path. The conducting path 607 is suitably connected to the same current source as the drive coils 605*a*, 605*b*, 605*c*, 605*d*, although in other embodiments a separate current source may be provided. Current passing along the conducting path 607 in an azimuthal direction at an off-centre position along the probe axis 602 (as indicated by the solid arrow 613) contributes to a balancing magnetic field, which induces a balancing voltage in at least one of the sense coils 603*a*, 603*b*. Current in an axial direction and current flowing azimuthally at the midpoint between the two sense coils 604*a*, 604*b* does not contribute to the balancing magnetic field. The conducting path 607 is arranged such that it induces a balancing voltage that at least partially offsets any baseline voltage across the sense coils 604*a*, 604*b* generated by the drive coils 605*a*, 605*b*, 605*c*, 605*d*.

As disclosed hereinabove, the conductive path 607 may suitably be provided by a balancing voltage taring device comprising at least one arcuate conductor which extends azimuthally around the probe axis 602. The balancing field is determined by the azimuthal length of the conducting path 607.

FIGS. 8(*b*)-8(*d*) are a series of schematic diagrams which illustrate the effect of varying the azimuthal length of a conducting path 707*a*, 707*b*, 707*c* interposed between two sets of coils 704*a*, 704*b* arranged coaxially on a longitudinal probe axis 702 for use in a susceptibility probe according to the present disclosure. The sets of coils 704*a*, 704*b*, which are similar to those described above with reference to FIG. 8(*a*), comprise a first set of coils 704*a* and a second set of coils 704*b*. Each set of coils 704*a*, 704*b* comprises a pair of spaced drive coils 705*a*, 705*c*; 705*b*, 705*d* and a sense coil 703*a*; 703*b* which is interposed between the respective drive coils 705*a*, 705*c*; 705*b*, 705*d*. A balancing voltage taring device (not shown) is interposed between the sets of coils 704*a*, 704*b* to define the conducting path 707*a*, 707*b*, 707*c*, which comprises first and second circumferentially extending conductors and two conducting bridges which extend between the circumferential conductors in a direction substantially parallel to the probe axis 702. As in FIG. 8(*a*), the conducting path 707*a*, 707*b*, 707*c* is shown in FIGS. 8(*b*) to 8(*d*) respectively as a complete circuit for illustrative purposes, but in practice the taring device includes terminals for connecting the conducting path to a current source for driving current through the conductive path.

FIG. 8(*b*) shows a conducting path 707*a* that spans only a short azimuthal distance around the probe axis 702. An off-centre portion of the conducting path 707 extending the circumferential direction indicated by the arrow 713 contributes to the balancing magnetic field. FIG. 8(*c*) shows a conducting path 707*b* that spans a greater azimuthal distance around the probe axis 702. This may be achieved, for example, by connecting a different land 411; 511 in a taring device of the kind described above with reference to FIGS. 6(*a*) and FIG. 6(*b*) or FIG. 7 or by moving a conducting bridge to include greater lengths of the first and second conductors 409*a*, 409*b*; 509*a*, 50*b* in the conducting path 707*b*. The conducting path 707*b* generates a stronger balancing magnetic field than the conducting path 707*a* of FIG. 8(*b*). Meanwhile, FIG. 8(*d*) shows a conducting path 707*c* that extends almost completely around the probe axis 702. This path may be formed, for example, by connecting lands 411; 511 at the ends of first and second conductors 409*a*, 409*b*; 509*a*, 509*b* in a taring device of the kind described above with reference to FIGS. 6(*a*) and FIG. 6(*b*) or FIG. 7 or by positioning a conducting bridge at or proximate ends of first and second circumferential conductors remote from connecting terminals, thereby to include substantially the entire lengths of the conductors in the conducting path. This conducting path 707*c* generate a stronger balancing magnetic field than the conducting path 707*b* of FIG. 8(*c*).

Figure 9:
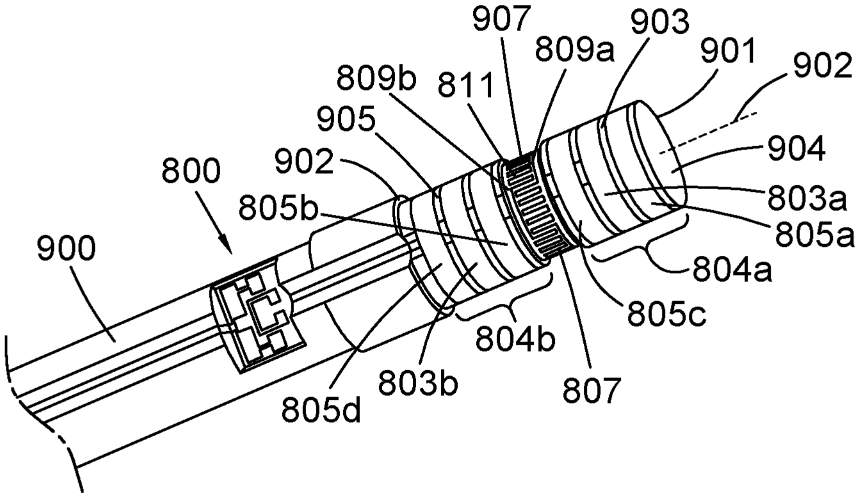
FIG. 9 is a perspective view of part of a probe according to yet another embodiment of the present disclosure, comprising two sets of coils and a taring device interposed therebetween on a mandrel.

FIG. 9 is a perspective view of a distal end portion of a probe 800 according to an embodiment of the present disclosure. The probe 800 comprises a coil arrangement as described in more detail below that is supported on a mandrel 901 fixedly secured to a distal end 902 of a wand 900. The wand 900 is adapted for connection to a suitable base station (not shown) comprising a signal processor. The probe 800 is typically connected to the base station by a wired connection through the wand 900, but in some embodiments may be connected wirelessly.

The mandrel 901 defines a longitudinal axis 902, comprising a first distal cylindrical portion 903 having a diameter of about 10 mm, which supports a first set of coils 804*a* proximate a distal sensing end 904 of the probe 800, a second proximal cylindrical portion 905, which similarly dimensioned to the distal portion 903 and supports a second set of coils 804*b* that is axially spaced relative to the first set of coils 804*a*, and a narrower cylindrical intermediate portion 907, which supports a balancing voltage taring device 807 between the first and second sets of coils 804*a*, 804*b*. The mandrel 901, with the coil arrangement fixedly mounted thereon, is received within a substantially cylindrical hollow probe housing (not shown) having an outer diameter of about 12 mm.

The first set of coils 804*a* comprises a first pair of drive coils 805*a*, 805*c* and a first sense coil 803*a* interposed between the drive coils 805*a*, 805*c*. The second pair of coils 805*b*, 805*d* similarly comprises a second pair of drive coils 805*b*, 805*d* and a second sense coil 803*b* interposed between the drive coils 805*b*, 805*d*.

The drive coils 805*a*, 805*c*; 805*b*, 805*d* within each set of coils 804*a*, 804*b* are substantially identical to one another. Each drive coil comprises between about 10 and about 60 turns of wire and has an outer radius of between about 1.5 mm and about 6 mm and an axial length of between about 0.5 mm and about 2.5 mm.

The sense coil 803*a*; 803*b* of each set of coils 804*a*, 804*b* comprises between about 100 and about 500 turns of wire and has an axial length of between about 0.75 mm and about 2 mm and a mean radius of between about 1.5 mm and about 6.5 mm. In the present embodiment, each sense coil 803*a*, 803*b* has a similar mean radius to the mean radius of the drive coils 805*a*, 805*c*; 805*b*, 805*d* of the respective set of coils 804*a*, 804*b*.

Each sense coil 803*a*; 803*b* is formed from wire having a diameter of between about 0.025 mm and 0.1 mm.

The coils are configured and arranged such that the distance between the centre of each sense coil 803*a*; 803*b* and the centre of each drive coil 805*a*, 805*c*; 805*b*, 805*d* within the same set of coils 804*a*; 804*b* is between about 1 mm and about 3 mm.

The total axial distance spanned by the first and second sets of coils 804*a*, 804*b* is between about 19 mm and about 30 mm. Meanwhile, the axial separation between the sense coils 803*a*, 803*b* of the first and second sets of coils 804*a*, 804*b* is between about 12 mm and about 15 mm.

In the present embodiment, the spacing between the first and second sets of coils 804*a*, 804*b* is about 12 mm in a direction parallel to the probe axis 902, but it will be understood that in other embodiments a different spacing between the coil sets 804*a*, 804*b* may be used.

The balancing voltage taring device 807 is substantially as described above with reference to FIGS. 6(*a*) and 6(*b*), comprising a flexible printed circuit board which is etched to form two substantially parallel elongate copper traces thereon which form first and second arcuate conductors 809*a*, 809*b* that extend azimuthally partially around the probe axis 902. The flexible circuit board is wrapped circumferentially around and fastened to the intermediate portion 907 of the mandrel 901, such that the first and second conductors 809*a*, 809*b* extend azimuthally around the probe axis 902 as shown in FIG. 9. One of the conductors 809*a* extends circumferentially around the mandrel 901 at an off-centre position between the first and second sets of coils 804*a*, 804*b*, more particularly between the first and second sense coils 803*a*, 803*b*, in a direction parallel to the axis 902 of the mandrel 901. The other conductor 809*b* extends circumferentially around the mandrel 901 at a point equidistant from the first and second sets of coils 804*a*, 804*b*, more particularly from the first and second sense coils 803*a*, 803*b*. In other arrangements, both conductors 809*a*, 809*b* may be positioned away from the midpoint between the sets of coils 804*a*, 804*b*, but they should be asymmetrically arranged with respect to the midpoint. In the present embodiment, each of the elongate conductors 809*a*, 809*b* extends in a respective plane that is substantially perpendicular to the axis 902 of the mandrel 901. In other embodiments, one of both conductors 809*a*, 809*b* may have a different configuration such that they also extend in a direction parallel to the axis 902, provided that at least one of the conductors 809*a*, 809*b* extends azimuthally around the axis 902 with an average off-centre location along the axis 902.

As described above, the first and second conductors 809*a*, 809*b* are formed with a plurality of lands 811 at a series of azimuthal positions around the probe axis 902, which lands 811 extend in a direction substantially parallel to the probe axis 902 between the conductors 809*a*, 809*b*. Each land 811 extends from one of the conductors 809*a*, 809*b* and terminates just short of the other conductor 809*b*, 809*a*. Each of the conductors 809*a*, 809*b* has a terminal (not shown) at one end for connection to a current source, and the conductors 809*a*, 809*b* are interconnected at one of the lands 811 to form a continuous conducting path through the first and second conductors 809*a*, 809*b*, as described in more detail below.

The drive coils 805*a*, 805*b*, 805*c*, 805*d* are connected in series with each other, while the first and second sense coils 803*a*, 803*b* are connected in anti-series. In an alternative arrangement the sense coils 803*a*, 803*b* may be connected in series but formed with opposite windings. The sense coils 803*a*, 803*b* are provided with connectors for connecting to the signal processor as described herein for processing a sense voltage detected by the sense coils to calculate the distance between the probe 800 and a magnetic marker. The drive coils 805*a*, 805*b*, 805*c*, 805*d* and the taring device 807 are connected to an AC current source. The first pair of drive coils 805*a*, 805*c* generate a driving magnetic field and induce a voltage in the first sense coil 803*a*. The second pair of drive coils 805*b*, 805*d* also generate a driving magnetic field and generate an approximately equal and opposite voltage in the second sense coil 803*b*. The net voltage induced in the first and second sense coils 803*a*, 803*b* from the first pair of drive coils 805*a*, 805*c* and the second pair of drive coils 805*b*, 805*d* is close to zero, but is unlikely to be exactly zero as a result of manufacturing tolerances and differences between the first set of coils 804*a* and the second set of coils 804. A residual baseline voltage typically therefore results. In use, a magnetic marker present in the driving magnetic field generates a response field which induces a sense voltage in one or both sense coils 803*a*, 803*b*. Typically, the marker is located distally of the tip 904 of the probe 800 such that the sense voltage is generated predominantly in the first sense coil 803*a* of the first distal set of coils 804*a*. The baseline voltage arising from the drive coils tends to mask the sense voltage from the marker and it is therefore desirable to minimise the baseline voltage as much as possible, so that the sense voltage is attributed predominantly to the response field and is indicative of the distance between first sense coil 803*a* and the marker, such that the signal processor can process the sense voltage to determine the distance and generate an output signal representing the distance.

Figure 10:
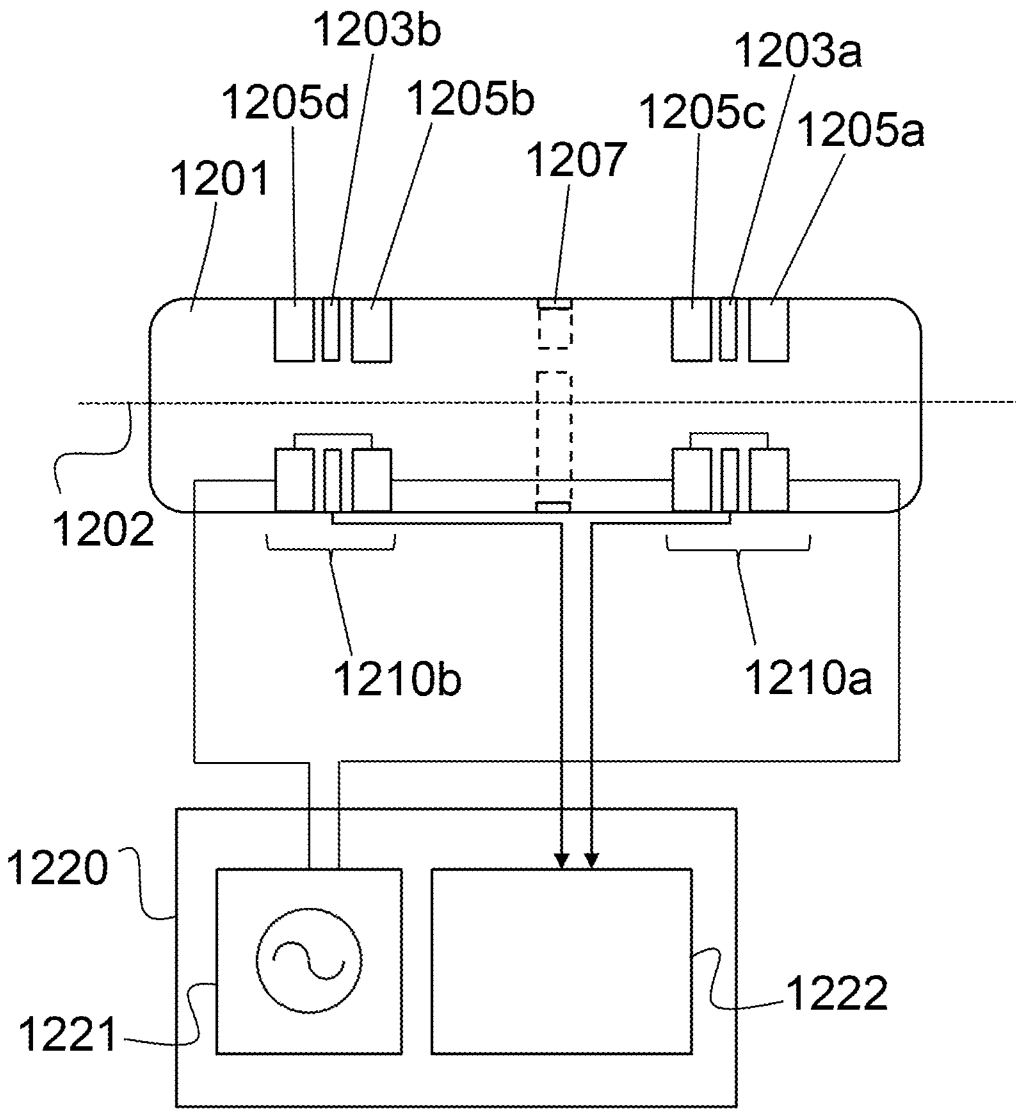
FIG. 10 is schematic diagram of a general arrangement of detection apparatus according to yet another embodiment of the present disclosure which comprises a probe including a mandrel of the kind shown in FIG. 5 with two sense coils in which a sense voltage is output separately from each sense coil to a signal processor.

Passing current through the conducting path of the taring device 807 generates a balancing magnetic field as disclosed herein. The strength of the balancing field depends on the azimuthal length of the conducting path, which can be controlled by selecting where to interconnect the first and second conductors 809*a*, 809*b*. Since one of the conductors 809*a*, 809*b* is positioned off-centre between the sets of coils 804*a*, 804*b* as described above, the balancing field induces unequal voltages in the first and second sense coils 803*a*, 803*b*, thereby producing a net balancing voltage which serves to offset at least partially the baseline voltage. The magnitude of the balancing field can thus be tuned to minimise the residual baseline voltage resulting from the drive coils 805*a*, 805*b*, 805*c*, 805*d* by correctly setting the azimuthal length of the conducting path. As will be apparent to those skilled in the art, this is achieved by forming a conducting bridge between a land 811 on one of the conductors 809*a*, 809*b* and the other conductor 809*b*, 809*a* at an azimuthal location such that the azimuthal length of the conducting path is such that current flowing in circumferential direction in the conductive path off-centre from the midpoint between the first and second sets of coils 804*a*, 804*b* induces a balancing voltage in the first and second sense coils 803*a*, 803*b* such that the baseline voltage is minimised, thereby allowing a sense voltage induced in one or both sense coils 803*a*, 803*b* from a response field generated by a magnetic marker in the driving field to be detected with improved sensitivity and accuracy In a variation of the arrangements described above with reference to FIGS. 3-5, 8(*a*) to 8(*d*) and 9, instead of connecting two sense coils in anti-series (or in series with opposite windings), two sense coils may be adapted for connection separately to the signal processor. FIG. 10 shows a mandrel 1201 for a probe which is similar to the mandrel 201 described above with reference to FIG. 5. However, it will be understood that this is purely for the purpose of illustration, and any other embodiment in accordance with the present disclosure may be similarly configured.

Thus, the mandrel 1201 of FIG. 10 comprises two sets of coils 1210, 1210, which are supported on the mandrel 1201 coaxially with a longitudinal axis 1202 of the mandrel. Each set of coils comprises two axially spaced drive coils 1205*a*, 1205*c*; 1205*b*, 1205*d* and a sense coil 1203*a*; 1203*b* which is interposed between its respective drive coils. A balancing voltage taring device 1207 is also supported on the mandrel 1201 intermediate the two sets of coils 1210*a*, 1210*b*. The drive coils 1205*a*, 1205*c*; 1205*b*, 1205*d* are connected in series to an AC current source 1221 which is housed within a base station 1220. Each sense coil 1203*a*, 1203*b* is connected separately to a signal processor 1222 within the base station. In this way, a baseline voltage induced directly in one of the sense coils 1203*a*, 1203*b* by the driving magnetic field can be used by the signal processor 1222 to remove from a voltage induced in the other sense coil 1203*b*, 1203*a* a corresponding baseline voltage component which is caused directly by the driving magnetic field, leaving only a sense voltage component which arises from a response field generated by a magnetic marker in the driving field and any residual baseline voltage. The taring device 1207 of the kind hereinbefore described can then be employed to minimise the residual baseline voltage in accordance with the present disclosure.

Figure 11:
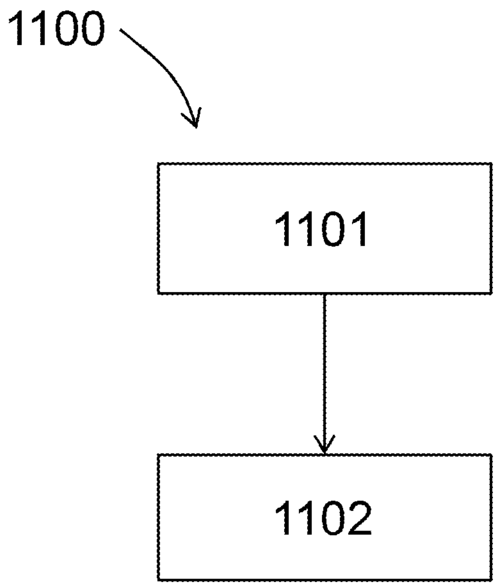
FIG. 11 is a flowchart showing a method of manufacturing a probe, according to yet another embodiment of the present disclosure.

FIG. 11 is a flowchart of a method 1100 of manufacturing a probe for sensing a magnetic marker according to another embodiment of the present disclosure. In a first step 1101, the method comprises mounting at least two first coils and at least one second coil substantially coaxially on a longitudinal axis of the probe, the at least two first coils being one of sense coils or drive coils and the at least one second coil being the other of a drive coil or sense coil, such that the one or more drive coils are connectable to a current source to generate a driving magnetic field through the one or more drive coils, and the one or more sense coils are connectable to a signal processor for processing one or more sense voltages induced in the respective one or more sense coils to generate an output signal; the first or second coils being configured or arranged to minimise a baseline voltage component of the sense voltage induced in the one or more sense coils that is attributable directly to the driving magnetic field; whereby the first and second coils are configured and arranged as a gradiometer for measuring the proximity of a magnetic marker to the probe and the output signal represents the distance between the marker and the probe.

In a second step 1102, the method comprises fitting to the probe a baseline voltage taring device comprising a first elongate conductor such that the first conductor defines a conducting path extending partially around the probe axis juxtaposed the one or more sense coils and is connectable to a current source to generate a balancing magnetic field in the vicinity of the one or more sense coils, such that in use the balancing magnetic field induces a balancing voltage in the one or more sense coils which at least partially offsets the baseline voltage; whereby the sense voltage is at least predominantly attributable to a response field generated by the marker in response to the driving field, which corresponds to the proximity of the marker.

In an alternative embodiment, in the first step 1101, the two or more sense coils may be arranged to output to the signal processor separate sense voltages to allow the signal processor to process the sense voltages to minimise a baseline voltage component of the sense voltages that is attributable directly to the driving magnetic field.

Step 1102 may optionally comprise adjusting the azimuthal length of the conducting path around the probe to minimise the baseline voltage across the one or more sense coils.

Although aspects of the present disclosure have been described with reference to particular embodiments, it is to be understood that these embodiments are merely illustrative of the principles and applications of the disclosure. It is therefore to be understood that numerous modifications may be made to the illustrative embodiments and that other arrangements may be devised without departing from the scope of the disclosure as defined by the appended claims.

It will be appreciated by those of ordinary skill in the art that features of these example embodiments may be combined in other embodiments that fall within the scope of the present disclosure.

While various details have been set forth in the foregoing description, it will be appreciated that the various aspects of the techniques for operating a diagnostic and/or surgical guidance system suitable for identifying, localizing, tracking, and detecting position of one or more implanted markers may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

Whilst in the foregoing description, integers or elements are mentioned which have known obvious or foreseeable equivalents, then such equivalents are herein incorporated as if individually set forth. Reference should be made to the claims for determining the true scope of the present disclosure, which should be construed as to encompass any such equivalents. It will also be appreciated by the reader that integers or features of the disclosure that are described as advantageous, convenient or the like are optional, and do not limit the scope of the independent claims. Moreover, it is to be understood that such optional integers or features, whilst of possible benefit in some embodiments of the disclosure, may not be desirable and may therefore be absent in other embodiments.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices of the base station or the one or more processors or microprocessors operative therein (e.g. floppy disk, hard disk drive, caches, random access memory, and other optical and magnetic storage devices and media). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states. The various methods steps disclosed herein may be implemented or programmed as algorithms, data structures, and instructions that may operate upon inputs from data channels and generate outputs that contain various types of data such as user actional data, user feedback signals, information, and images.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, processor-based base station, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analogue or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analogue communication medium (e.g., a fibre optic cable, a waveguide, a wired communications link, a wireless communication link (e.g., transmitter, receiver, transmission logic, reception logic, etc.), etc.).

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

The use of headings and sections in the application is not meant to limit the disclosure;

each section can apply to any aspect, embodiment, or feature of the disclosure. Only those claims which use the words "means for" are intended to be interpreted under 35 USC 112, sixth paragraph, and even then only in the United States. Absent a recital of "means for" in the claims, such claims should not be construed under 35 USC 112. Outside the United States, the words "means for" are intended to have their natural meaning. Limitations from the specification are not intended to be read into any claims, unless such limitations are expressly included in the claims.

Embodiments disclosed herein may be embodied as a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, embodiments may take the form of a computer program product embodied in one or more computer readable medium(s) having computer readable program code embodied thereon.

Although aspects of the invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the scope of the invention as defined by the appended claims.

The invention claimed is:

1. A probe for locating a magnetic marker for use in surgery, the probe comprising:

at least two first coils and at least one second coil which are arranged substantially coaxially on a longitudinal axis of the probe as a gradiometer for measuring a proximity of the magnetic marker to the probe; the at least two first coils being one of either sense coils or drive coils, and the at least one second coil being the other of a drive coil or sense coil; the one or more drive coils being adapted for connection to a current source to generate a driving magnetic field, and the one or more sense coils being adapted for connection to a signal processor for processing one or more sense voltages induced in the respective one or more sense coils to generate an output signal representing a distance between the marker and the probe; the first coils or the second coil being configured or arranged to minimize a baseline voltage component of the one or more sense voltages induced in the respective one or more sense coils that is attributable directly to the driving magnetic field or to output to the signal processor separate sense voltages of the one or more sense voltages from respective two or more sense coils of the one or more sense coils to allow the signal processor to process the one or more sense voltages to minimize a baseline voltage component of the one or more sense voltages that is attributable directly to the driving magnetic field; and a baseline voltage taring device comprising a first elongate conductor which defines a conducting path that extends azimuthally, but incompletely around the longitudinal axis of the probe juxtaposed with the one or more sense coils, and is connectable to the current source or another current source to generate a balancing magnetic field in a vicinity of the one or more sense coils;

wherein the conducting path is configured and arranged such that in use the balancing magnetic field induces a balancing voltage in the one or more sense coils that at least partially offsets the baseline voltage component; whereby the one or more sense voltages are at least predominantly attributable to a response field generated by the marker in response to the driving field, which corresponds to the proximity of the marker.

2. The probe according to claim 1, comprising a first set of coils comprising the at least two sense coils of the one or more sense coils that are separated from each other along the longitudinal axis of the probe and a drive coil of the one or more drive coils interposed between the at least two sense coils of the one or more sense coils.

3. The probe according to claim 2, comprising a second set of coils, the second set of coils comprising at least one additional drive coil and at least one additional sense coil; wherein the first set of coils and the second set of coils are separated from each other along the longitudinal axis of the probe.

4. The probe according to claim 3, wherein the first set of coils comprises a first sense coil of the one or more sense coils interposed between a first pair of drive coils of the one or more drive coils; wherein the second set of coils comprises a second sense coil of the at least one additional sense coil interposed between a second pair of drive coils of the at least one additional drive coils.

5. The probe according to claim 3, wherein the first elongate conductor is disposed at a fixed axial position between the first set of coils and the second set of coils.

6. The probe according to claim 2, wherein the at least two sense coils of the one or more sense coils are connected in anti-series with each other or have opposite windings, thereby to minimize the baseline voltage component of the one or more sense voltages induced in the respective at least two sense coils of the one or more sense coils that is attributable directly to the drive magnetic field.

7. The probe according to claim 2, wherein the at least two sense coils of the one or more sense coils are adapted for individual connection to the signal processor such that the signal processor can process the one or more sense voltages induced in the respective at least two sense coils of the one or more sense coils to minimize the baseline voltage component of the one or more sense voltages that is attributable directly to the driving magnetic field.

8. The probe according to claim 1, further comprising at least two drive coils of the one or more drive coils that are axially separated from each other along a length of the longitudinal axis of the probe and a sense coil of the one or more sense coils interposed between the at least two drive coils of the one or more drive coils;

wherein the at least two drive coils of the one or more drive coils are connected in anti-series with each other or have opposite windings, thereby to minimize the baseline voltage component of the one or more sense voltages induced in the one or more sense coils that is attributable directly to the drive magnetic field.

9. The probe according to claim 1, wherein the taring device further comprises a second conductor and at least one conducting bridge extending between the first elongate conductor and the second conductors, which defines an azimuthal length of the conducting path.

10. The probe according to claim 9, wherein the first elongate conductor and the second conductors are defined by two conducting loops which each extend around the longitudinal axis of the probe.

11. The probe according to claim 9, wherein one or both of the first elongate conductor and the second conductors comprise a plurality of lands at a series of azimuthally spaced positions around the longitudinal axis of the probe for connecting the at least one conducting bridge, thereby to define the conducting path.

12. The probe according to claim 1, wherein the first elongate conductor comprises a conductive trace and/or wire.

13. The probe according to claim 1, wherein the taring device further comprises a flexible circuit board that is wrapped circumferentially around the longitudinal axis of the probe.

14. The probe according to claim 1, wherein the taring device further comprises a flexible printed circuit board comprising at least one conductive trace defining the first conductor.

15. The probe according to claim 1, further comprising:

a detection apparatus for locating the magnetic marker during surgery, the apparatus comprising:

the current source or the another current source which is selectively operable to generate the driving magnetic field through the one or more drive coils and the first elongate conductor;

the signal processor or another signal processor configured to receive one or more sense voltages from the one or more sense coils and generate an output signal representing the distance between the probe and the magnetic marker; and optionally wherein the magnetic marker is implantable.

16. A method of manufacturing a probe for sensing a magnetic marker during a surgical procedure, the method comprising:

mounting at least two first coils and at least one second coil substantially coaxially on a longitudinal axis of the probe, the at least two first coils being one of sense coils or drive coils and the at least one second coil being the other of a drive coil or sense coil, such that the one or more drive coils are connectable to a current source to generate a driving magnetic field through the one or more drive coils, and the one or more sense coils are connectable to a signal processor for processing one or more sense voltages induced in the respective one or more sense coils to generate an output signal; the first coils or the second coil being configured or arranged to minimize e-a baseline voltage component of the one or more sense voltages induced in the respective one or more sense coils that is attributable directly to the driving magnetic field or to output to the signal processor separate sense voltages of the one or more sense voltages from respective two or more sense coils of the one or more sense coils to allow the signal processor to process the one or more sense voltages to minimize a baseline voltage component of the one or more sense voltages that is attributable directly to the driving magnetic field;

whereby the first coils and the second coil are configured and arranged as a gradiometer for measuring a proximity of the magnetic marker to the probe and the output signal represents a distance between the marker and the probe;

fitting to the probe a baseline voltage taring device comprising a first elongate conductor such that the first conductor defines a conducting path that extends azimuthally but incompletely around the longitudinal axis of the probe juxtaposed with the one or more sense coils, and is connectable to the current source or another current source to generate a balancing magnetic field in a vicinity of the one or more sense coils, such that in use the balancing magnetic field induces a balancing voltage in the one or more sense coils which at least partially offsets the baseline voltage component; whereby the one or more sense voltages are at least predominantly attributable to a response field generated by the marker in response to the driving field, which corresponds to the proximity of the marker.

17. The method according to claim 16, further comprising adjusting an azimuthal length of the conducting path around the probe to minimize the baseline voltage across the one or more sense coils.

18. A method of setting up a probe for sensing a magnetic marker for use in surgery, the probe comprising:

at least two first coils and at least one second coil which are arranged substantially coaxially on a longitudinal axis of the probe as a gradiometer for measuring a proximity of the magnetic marker to the probe; the at least two first coils being one of either sense coils or drive coils, the at least one second coil being the other of a drive coil or sense coil; the one or more drive coils being adapted for connection to a current source to generate a driving magnetic field, and the one or more sense coils being adapted for connection to a signal processor for processing a sense voltage induced in the one or more sense coils to generate an output signal; the first coils or the second coil being configured or arranged to minimize a baseline voltage component of the one or more sense voltages induced in the respective one or more sense coils that is attributable directly to the driving magnetic field or to output to the signal processor separate sense voltages of the one or more sense voltages from respective two or more sense coils of the one or more sense coils to allow the signal processor to process the one or more sense voltages to minimize a baseline voltage component of the one or more sense voltages that is attributable directly to the driving magnetic field;

a baseline voltage taring device comprising a first elongate conductor which defines a conducting path extending partially around the longitudinal axis of the probe juxtaposed with the one or more sense coils, and is connectable to the current source or another current source to generate a balancing magnetic field in the vicinity of the one or more sense coils;

the method comprising adjusting an azimuthal length of the conducting path around the longitudinal axis of the probe to control the balancing magnetic field to induce a balancing voltage across the one or more sense coils which at least partially offsets the baseline voltage component.

* * * * *